(12) United States Patent
Miyazaki et al.

(10) Patent No.: US 7,384,790 B2
(45) Date of Patent: Jun. 10, 2008

(54) METHOD OF ANALYZING PEPTIDE FOR DETERMINING C-TERMINAL AMINO ACID SEQUENCE

(75) Inventors: Kenji Miyazaki, Minato-ku (JP); Akira Tsugita, Chuo-ku (JP); Naoyuki Takahashi, Chuo-ku (JP); Takuji Nabetani, Chuo-ku (JP); Toshimasa Yamazaki, Minato-ku (JP); Kenichi Kamijo, Minato-ku (JP)

(73) Assignee: NEC Corporation, Tokyo (JP)

( * ) Notice: Subject to any disclaimer, the term of this patent is extended or adjusted under 35 U.S.C. 154(b) by 722 days.

(21) Appl. No.: 10/489,198

(22) PCT Filed: Mar. 24, 2003

(86) PCT No.: PCT/JP03/03512

§ 371 (c)(1),
(2), (4) Date: Mar. 10, 2004

(87) PCT Pub. No.: WO03/081255

PCT Pub. Date: Oct. 2, 2003

(65) Prior Publication Data

US 2005/0074832 A1    Apr. 7, 2005

(30) Foreign Application Priority Data

Mar. 25, 2002 (JP) ............................ 2002-083311

(51) Int. Cl.
*G01N 33/68* (2006.01)
*G01N 33/483* (2006.01)
*G01N 27/12* (2006.01)

(52) U.S. Cl. ...................... 436/90; 436/86; 436/89; 435/23

(58) Field of Classification Search ............... 436/86, 436/89, 90; 530/345; 435/23
See application file for complete search history.

(56) References Cited

U.S. PATENT DOCUMENTS 5,521,097 A * 5/1996 Uchida et al. ............... 436/86
6,046,053 A * 4/2000 Tsugita et al. .............. 436/89

FOREIGN PATENT DOCUMENTS

| EP | 0 905 519 A1 * | 3/1999 |
| JP | 05-52852 A | 3/1993 |
| JP | 10-293130 A | 11/1998 |

OTHER PUBLICATIONS

Tsugita, Akira, Development of Carboxyl-Terminal Sequencing Methods for Proteins and Peptide by the use of FAB Mass Spectrometry and Perfluoric Acid, 1997, Journal of the Mass Spectrometry Society of Japan, 45(5), 561-589.*

(Continued)

*Primary Examiner*—Walter D. Griffin
*Assistant Examiner*—Christine T Mui
(74) *Attorney, Agent, or Firm*—Sughrue Mion, PLLC

(57) ABSTRACT

The present invention provides a method for analyzing the C-terminal amino acid sequence of a peptide by applying reaction technique for successively releasing the C-terminal amino acids therefrom, which method can suppress, when releasing the C-terminal amino acids of the peptide in sequence, such as an undesirable side reaction as cleavage of peptide bond in the intermediate position of the peptide, and allows to carry out the chemical treatment thereof under widely applicable conditions. In the method according to the present invention, an alkanoic acid anhydride and a perfluoroalkanoic acid both of vapor phase, which are supplied from a mixture containing an alkanoic acid anhydride with a small amount of a perfluoroalkanoic acid added thereto, are allowed to act on a dry sample of the peptide to be examined in a dry atmosphere at a temperature chosen in a range of 15 to 60° C.; whereby the release of the C-terminal amino acid is resulted from successive formation of a 5-oxazolone structure being followed by cleavage of the 5-oxazolone ring; and then the C-terminal amino acids sequence is identified by analysis based on the decrease in molecular weight in a series of the reaction products obtained.

18 Claims, 4 Drawing Sheets

OTHER PUBLICATIONS

Mobile Phase Studies (Polar Modifiers), Jan. 15, 2004, Virginia Tech, 91-110.*

Miyazaki, Kenji et al. C-terminal sequencing method for peptides and proteins by the reacion with a vapor perfluoric acid in acetic anhydride, 2004, Proteomics, 4, pp. 11-19.*

K. Takamoto et al., "Carboxy-terminal degradation of peptides using perfluoroacyl anhydrides A C-terminal sequencing method", *Eur. J. Biochem.*, vol. 228, 1995, pp. 362-372.

A. Tsugita et al., "C-terminal sequencing of protein—A novel partial acid hydrolysis and analysis by mass spectrometry", *Eur. J. Biochem.*, vol. 206, 1992, pp. 691-296.

A. Tsugita et al., "Reaction of Pentafluoropropionic Anhydride Vapor on Polypeptide as Revealed by Mass Spectrometry. A Carboxypeptidase Mimetic Degradation", *Chemistry Letters*, The Chemical Society of Japan, 1992, pp. 235-238.

* cited by examiner

Fig. 1

| Pretreatment | Main Reaction | Post-treatment |
|---|---|---|
| Peptide → CH₃CO-Peptide → Dry up | → → (CH₃CO)ₙ-Peptide(dehydro) | → → Truncated → MALDI- Dry up CH₃CO-Peptide Dry up TOF-MS |
| 5% CH₃COOH 95% (CH₃CO)₂O (+1% Pyridine) 50° C, 1 h | 1-20% CF₃(CF₂)ₙCOOH 80-99% (CH₃CO)₂O 20-60° C, 1-16 h N=0, 1, 2 | 1-20% DMAE aq. 60-100° C, 0.5-2 h or 10% Pyridine aq. 100° C, 0.5 h |

METHOD OF ANALYZING PEPTIDE FOR DETERMINING C-TERMINAL AMINO ACID SEQUENCE

TECHNICAL FIELD

The present invention relates to a method for analysis of C-terminal amino acid sequence of peptide, more particularly to a method comprising steps of releasing the C-terminal amino acids of the peptide successively by chemical means, determining the molecular weights of the obtained reaction products by mass spectrometry, and clarifying the C-terminal amino acid sequence as for the peptide, based on the observed decreases in molecular weight that are caused by a series of amino acids eliminated successively. The present invention further relates to a kit, which is used exclusively for the above method for analysis, for treatment to prepare the reaction products to be subjected to mass spectrometry by treatment of releasing the C-terminal amino acids of the peptide successively by chemical means.

BACKGROUND ART

With respect to peptides and proteins collected from nature, the amino acid sequences identified thereof are essential information in course of studying the biological properties and functions of the peptides and proteins. Currently, the full-length amino acid sequences for peptides and proteins are determined as deduced amino acid sequences, based on corresponding gene information thereof, that is, nucleotide sequences of c-DNAs produced from genomic genes or m-RNAs which encode their peptides. However, in identifying the c-DNAs produced from the genomic gene or m-RNA which encodes the peptide, the knowledge of partial amino acid sequences of the peptides is still required.

It is generally considered that, as the knowledge of the partial amino acid sequences of peptide, the N-terminal amino acid sequence and C-terminal amino acid sequence of peptide are particularly useful. Specifically explaining, for example, in selecting a c-DNA which encodes an intended peptide from a c-DNA library prepared from a large number of m-RNAs, if the N-terminal amino acid sequence and C-terminal amino acid sequence thereof are known, the aimed c-DNA can be selected by using nucleic acid probes that are produced based on the above amino acid sequences of the two terminals. Or, the aimed c-DNA can be amplified selectively by applying PCR with use of oligonucleotide primers that are produced based on the amino acid sequences of the two termini.

As the method for analyzing the N-terminal amino acid sequence of a peptide, there has been conventionally used a method of allowing an acid to act on a peptide to release the N-terminal amino acids successively by hydrolysis and identifying the amino acids resulted therefrom. Meanwhile, as the method for analyzing the C-terminal amino acid sequence of a peptide, there has been proposed a method of releasing the C-terminal amino acids thereof successively by chemical means and identifying the C-terminal amino acids released thereby, based on the molecular weight differences between the original peptide and truncated peptides that are obtained as reaction products therefrom. As the technique for releasing the C-terminal amino acids successively by chemical means, there is proposed, for example, a method comprising steps of allowing a vapor generated from a high concentration aqueous solution of pentafluoropropanoic acid ($CF_3CF_2COOH$) or a high concentration aqueous solution of heptafluorobutanoic acid ($CF_3CF_2CF_2COOH$), to act on a dried peptide under heating up condition at 90° C., and releasing the C-terminal amino acids by selective hydrolysis enhanced with use of said perfluoroalkanoic acid [Tsugita, A. et al., Eur. J. Biochem. 206, 691-696 (1992)]. There is also proposed a method comprising steps of using, in place of the above high concentration aqueous solution of a perfluoroalkanoic acid, an acetonitrile solution of pentafluoropropanoic acid anhydride [$(CF_3CF_2CO)_2O$] or an acetonitrile solution of heptafluorobutanoic acid anhydride [$(CF_3CF_2CF_2CO)_2O$], allowing a vapor generated form the solution, to act on a dried peptide under cooling down condition at such a low temperature, for example, at −18° C., and releasing the C-terminal amino acids selectively, which is forced with use of the perfluoroalkanoic acid anhydride [Tsugita, A. et al., Chem. Lett. 1992, 235-238; Takamoto K. et al., Eur. J. Biochem. 228, 362-372 (1995)].

In said technique for selectively releasing the C-terminal amino acids by allowing a perfluoroalkanoic acid or a perfluoroalkanoic acid anhydride, which are supplied as a vapor thereof, to act on a dried peptide, it has been reported that an oxazolone ring structure is once formed from the C-terminal amino acids as a reaction intermediate, in a dehydration reaction shown by the following reaction scheme (I):

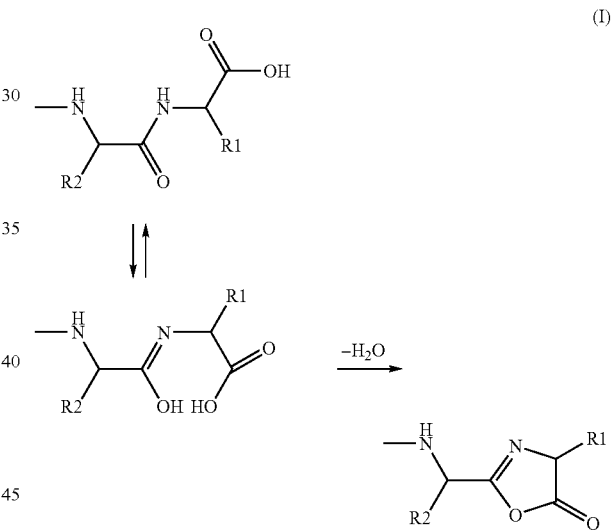

then, the perfluoroalkanoic acid acts on the oxazolone ring to give rise to a reaction shown by the following reaction scheme (II):

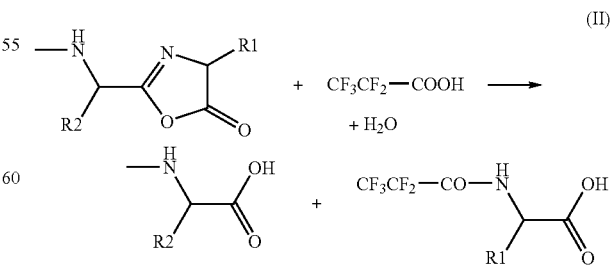

as a result, reaction of selectively releasing the C-terminal amino acid therefrom is achieved.

As the above reaction of selectively releasing the C-terminal amino acid proceeds successively, there is obtained, at a timing when a given treatment time has passed, a mixture comprising a series of reaction products in which one to ten odd amino acid residues have been removed from the C-terminal of the original peptide, respectively. This mixture comprising a series of reaction products is subjected to mass spectrometry to measure the masses of the ion species derived from the reaction products, whereby can be obtained a series of peaks exhibiting the mass differences, which reflect the C-terminal amino acid sequence. Specifically explaining, the individual reaction products are formed in reaction of successively releasing C-terminal amino acids from the original peptide; hence, for example, a set of reaction products including several members in series, where up to several amino acid residues have been removed from the original peptide, are subjected to mass spectrometry and, thereby, the masses of corresponding ion species thereto can be analyzed collectively, which enables determination of C-terminal amino acid sequence of such several amino acid residues at one time.

Incidentally, for example, the information of C-terminal amino acid sequence used in production of nucleic acid probe or primer may ordinarily be, in terms of the nucleotide sequence which codes such amino acid sequence, about 18 to 24 bases and accordingly about 6 to 8 amino acids. The identification of C-terminal amino acid sequence of up to ten odd amino acid residues is required only in very rare cases. Therefore, the above methods for preparation of treated sample comprising a series of reaction products, in which all the removals extending up to 10 amino acid residues are included, by the reaction of releasing the C-terminal amino acids from the dried peptide, where a vapor of a perfluoroalkanoic acid or a perfluoroalkanoic acid anhydride are supplied in vapor phase and allowed to act thereon, are suitable for the above-mentioned purposes.

DISCLOSURE OF THE INVENTION

The methods comprising such steps of supplying a vapor of a perfluoroalkanoic acid or a perfluoroalkanoic acid anhydride in vapor phase and allowing them to act on a dried peptide are useful means for clarifying the C-terminal amino acid sequence therein; however, for extending application of the methods as a general means for a wide use, the methods have been found to have the practical problems described below.

In the above-mentioned method with use of a high concentration aqueous solution of a perfluoroalkanoic acid, which allows a vapor of the perfluoroalkanoic acid to act on a dried peptide under heating up condition, for example, at 90° C., there occurs a side reaction in which, at the serine residue [—NH—CH(CH$_2$OH)—CO—] in the peptide, an N,O-acyl rearrangement reaction proceeds between the amino group (—NH—) on its α-position and the hydroxyl group (—OH) on its β-position, subsequently, hydrolysis proceeds, which results in cleavage of peptide taking place at the N-terminal of the serine residue. Depending upon the conditions used, there also occurs a side reaction in which, at the threonine reside [—NH—CH(CH(CH$_3$)OH)—CO—] having a hydroxyl group (—OH) on its β-position, hydrolysis proceeds based on a similar mechanism, which results in cleavage of peptide taking place at the N-terminal of the threonine residue. There further occurs a side reaction in which, at the aspartic acid residue [—NH—CH(CH$_2$COOH)—CO—] in the peptide, peptide bond rearrangement from C-terminal carboxy group to carboxy group on its β-position and subsequent hydrolysis proceed, which results in cleavage of peptide taking place at the C-terminal of the aspartic acid residue.

When the cleavage of peptide due to such side reactions happens, selective release of C-terminal amino acids proceeds simultaneously even to the resulting N-terminal peptide fragments. On some occasions, the co-existence of reaction products that are originated from these side reactions may be a factor interfering with the accuracy in the measurement by mass spectrometry conducted toward intended reaction products.

Further, even when there occurs no cleavage of peptide but when there is formed a branched type peptide wherein the N-terminal portion of peptide is linked to the hydroxyl group (—OH) on the β-position thereof, which leads to loss of amide bond at the site, there is no formation of oxazolone ring structure therefrom, and accordingly selective release of C-terminal amino acid make no further progress thereafter.

Meanwhile, in the above-mentioned method with use of an acetonitrile solution of a perfluoroalkanoic acid anhydride, which allows a vapor of the perfluoroalkanoic acid anhydride generated from the solution to act on a dried peptide under cooling down condition, for example, at −18° C., no water molecule being vaporized from the solution is present in said system and, therefore, the method has such an advantage that the occurrence of the above-mentioned side reactions can be avoided effectively. However, since the reactivity of the perfluoroalkanoic acid anhydride used is high, effective suppression of undesired side reactions is more difficult when the treatment temperature rises higher; therefore, the treatment temperature is required to be kept at such a low temperature as, for example, −18° C. In other words, when the control of the treatment temperature is not enough, there is a high possibility that undesired side reactions are escalated thereby; therefore, in this view, the method still has somewhat weakness in the wide applicability and leaves a room to be improved further. In addition, when water condensation takes place in association with cooling, the resulting water gives rise to deterioration of the reagent used, i.e. deactivation of the perfluoroalkanoic acid anhydride used, which may result in a reduced reactivity on occasion, and thus there remains some anxiety that it may happen to become a serious problem in practical application.

The present invention solves the above-mentioned problems and aims at providing a method for reaction to release the C-terminal amino acids successively, with use of which method, when a reaction mechanism via formation of oxazolone ring structure as explained above is used to release the C-terminal amino acids from the peptide, undesired side reactions such as cleavage of peptide bond somewhere along the peptide chain can be easily suppressed and further said chemical treatment itself can be carried out under widely applicable conditions. More specifically, the aim of the present invention is to provide a method for analysis of C-terminal amino acid sequence of peptide, by using a novel means for reaction of releasing the C-terminal amino acids successively, which means can avoid side reactions such as cleavage in the middle of peptide, when successively releasing the C-terminal amino acids, and can carry out the chemical treatment itself therefor in mild temperature conditions near room temperature that do not need any precise temperature control with heating or cooling. Furthermore, the present invention ultimately aims at wide application of such a method for analysis of C-terminal amino acid sequence of peptide and, in more particular, aims at providing a kit for treatment of releasing the C-terminal amino acids successively according to said novel means for reaction of releasing the C-terminal amino acids from the peptide, which is exclusively used in the analysis method of the present invention.

The present inventors made an intensive study and examination continually in order to solve the above-mentioned problems. As a result, it was concluded that the undesired reactions seen in the case of the method, where a high concentration aqueous solution of a perfluoroalkanoic acid is used to allow a vapor of the perfluoroalkanoic acid therefrom to act on a dried peptide under heating up conditions, for example, at 90° C., occur because the vapor of a perfluoroalkanoic acid as well as water molecule, both vaporized from the high concentration aqueous solution of the perfluoroalkanoic acid, are present in the reaction system, for example, at the serine residue [—NH—CH(CH$_2$OH)—CO—] in the peptide, the N,O-acyl rearrangement reaction between the amino group (—NH—) on its α-position and the hydroxy group (—OH) on its β-position is promoted under said heating conditions and the hydrolysis of the ester formed thereby is also advanced by the help of water molecules co-existing in the reaction system. Meanwhile, in the case of the method, where an acetonitrile solution of a perfluoroalkanoic acid anhydride is used to allow a vapor of the perfluoroalkanoic acid anhydride therefrom to act on a dried peptide under cooling down conditions, for example, at −18° C., it has been confirmed that although there is no water molecule in the reaction system, such a high reactivity of the perfluoroalkanoic acid anhydride per se invites a rapid increase in the frequency of undesired side reactions relative to rising up of the treatment temperature.

Based on the above finding, the present inventors searched such reaction conditions as, without using any water solvent working as source for feeding water molecules to the reaction system and further without using any reagent with such high reactivity as perfluoroalkanoic acid anhydride, an oxazolone ring structure can be formed from the C-terminal amino acids of peptide, as an reaction intermediate and then reaction of selectively releasing the C-terminal amino acid can be completed in association with cleavage of the oxazolone ring. As a result, it was found that with use of a mixture obtained by adding a small amount of a perfluoroalkanoic acid to an alkanoic acid anhydride, when the perfluoroalkanoic acid and alkanoic acid anhydride, both of vapor phase, supplied from the mixture are allowed to act on a dried peptide, even at a treatment temperature such as 60° C. or less, the formation of oxazolone ring structure can be progressed, and subsequently followed by the reaction of selectively releasing the C-terminal amino acid therefrom, which is resulted from the cleavage of this oxazolone ring. It was also found that as the reactivity of alkanoic acid anhydride is significantly mild as compared with a perfluoroalkanoic acid anhydride, even in the co-presence of the perfluoroalkanoic acid, it is far from giving rise to any cleavage in the middle of peptide. Specifically explaining, the alkanoic acid anhydride acts, in the co-presence of the perfluoroalkanoic acid, on the hydroxy group present on the serine residue [—NH—CH(CH$_2$OH)—CO—] or threonine residue [—NH—CH(CH(CH$_3$)OH)—CO—] in the peptide to make progress preferentially in an O-acylation reaction, which leads to inhibiting the N,O-acyl rearrangement reaction competitively. It was also found that an N-acylation reaction to the amino group of N-terminal proceeds simultaneously and there also proceed, for example, an N-acylation reaction to the amino group on the ε-position of lysine residue [—NH—CH(CH$_2$CH$_2$CH$_2$CH$_2$NH$_2$)—CO—] and an O-acylation reaction to the phenolic hydroxy group of tyrosine reside [—NH—CH(CH$_2$—C$_6$H$_4$—OH)—CO—].

As a result, it was found that since the reactive functional groups such as hydroxy group or amino group on the side chain, which are involved in the rearrangement reaction such as N,O-acyl rearrangement reaction that initiates the cleavage in the middle of peptide, undergo protection and modification, undesired side reactions are avoided and, at a treatment temperature of, for example, 60° C. or less, there selectively proceed only reactions wherein the oxazolone ring structure is formed as the intended reaction intermediate from the C-terminal amino acid, and subsequently followed by the reaction of releasing the C-terminal amino acid in association with the cleavage of the oxazolone ring. Based on the above findings, the present inventors have been completed the present invention.

Hence, the method for analysis of C-terminal amino acid sequence of peptide according to the present invention is a method for analyzing the C-terminal amino acid sequence of a peptide to be examined, which method comprises steps of:

releasing the C-terminal amino acids in sequence from the peptide to be examined by chemical means to prepare a mixture containing a series of reaction products thereof, subjecting the series of reaction products and the original peptide to mass spectrometry to measure the decreases in molecular weight associated with the successive release of the C-terminal amino acid thereof, and identifying a series of the amino acids removed successively, based on a series of the decrease in the molecular weight measured and arranging the amino acids identified from the C-terminal to obtain the information of the C-terminal amino acid sequence of the peptide, wherein the technique of treatment used in the step of releasing the C-terminal amino acids is a means comprising steps of:

allowing an alkanoic acid anhydride and a perfluoroalkanoic acid both of vapor phase, which are supplied from a mixture containing an alkanoic acid anhydride with a small amount of a perfluoroalkanoic acid added thereto, to act on a dry sample of the peptide to be examined in a dry atmosphere at a temperature selected in a range of 15 to 60° C.; and carrying out the release of the C-terminal amino acid in association with the process that at the C-terminus of the peptide, the formation of a 5-oxazolone structure represented by the following general formula (III):

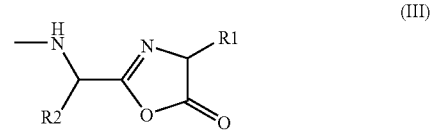

(III)

wherein R1 is a side chain of the C-terminal amino acid of the peptide, and R2 is a side chain of the amino acid residue positioned just before the C-terminal amino acid, is followed by the cleavage of the 5-oxazolone ring.

Further, as the alkanoic acid anhydride contained in said mixture obtained by adding a small amount of a perfluoroalkanoic acid to the alkanoic acid anhydride, there is preferably used a symmetric anhydride of an alkanoic acid having 2 to 4 carbon atoms. Among others, as said symmetric acid anhydride, a symmetric anhydride of a linear-chain alkanoic acid having 2 to 4 carbon atoms is preferred, and in particular, acetic anhydride is used suitably. Meanwhile, as said perfluoroalkanoic acid, there is preferably used a perfluoroalkanoic acid of which pKa is within the range of 0.3 to 2.5. As the perfluoroalkanoic acid, there can be suitably used, for example, a perfluoroalkanoic acid having 2 to 4 carbon atoms, and among the rest, a linear-chain perfluoroalkanoic acid having 2 to 4 carbon atoms is more adapted. In said mixture obtained by adding a small amount of the perfluoroalkanoic acid to the alkanoic acid anhydride, the content of the perfluoroalkanoic acid is selected desirably in a range of 1 to 20% by volume relative to the total volume of the alkanoic acid anhydride and the perfluoroalkanoic acid.

In the treatment using said mixture obtained by adding a small amount of the perfluoroalkanoic acid to the alkanoic acid anhydride, said dry atmosphere is preferably a state in which oxygen as well as water has been removed. In particular, the dry atmosphere is more preferably achieved inside an airtight vessel by vacuuming up the atmosphere inside it. Additionally, in the treatment using the mixture obtained by adding a small amount of the perfluoroalkanoic acid to the alkanoic acid anhydride, the temperature is more preferably set at a temperature selected in a range of 15 to 50° C.

In the analysis method of the present invention, in addition to the step of the treatment using said mixture obtained by adding a small amount of the perfluoroalkanoic acid to the alkanoic acid anhydride, hydrolysis treatment comprising steps of:

applying, to the mixture containing a series of reaction products, which is obtained in said step of releasing the C-terminal amino acids successively, a post-treatment of removing the residual alkanoic acid anhydride and perfluoroalkanoic acid therein in a dry state, then, feeding a basic, nitrogen-containing aromatic cyclic compound or a tertiary amine compound and water molecule both of vapor phase supplied by using an aqueous solution in which the basic, nitrogen-containing aromatic cyclic compound or a tertiary amine compound is dissolved, allowing the water molecule to act on the reaction products of peptide in the presence of said basic, nitrogen-containing organic compound, and after said treatment for hydrolysis, re-drying post-treatment which is conducted by removing the basic, nitrogen-containing organic compound and water molecule both remaining in the mixture containing a series of the reaction products, followed by drying.

Further in the analysis method of the present invention, in addition to the step of said treatment using the mixture obtained by adding a small amount of the perfluoroalkanoic acid to the alkanoic acid anhydride, the method may be provided, prior to the step of releasing the C-terminal amino acids successively, with an additional step for a pre-treatment of applying, to the N-terminal amino group of the peptide to be examined, N-acylation protection in advance with use of an acyl group derived from the alkanoic acid constituting said alkanoic acid anhydride.

The pretreatment step of applying N-acylation protection to the N-terminal amino group may be conducted by employing technique where the N-acylation for amino groups in the peptide is effected by allowing an alkanoic acid anhydride and an alkanoic acid both of vapor phase, which are supplied from a mixture obtained by adding a small amount of the alkanoic acid to the alkanoic acid anhydride, to act on a dried sample of the peptide to be examined in a dry atmosphere at a temperature selected in a range of 10 to 60° C. In such a case, as the alkanoic acid anhydride used in the pretreatment step of applying N-acylation protection to the N-terminus and as the alkanoic acid anhydride used in the step conducted thereafter of releasing the C-terminal amino acids successively, used may be the same alkanoic acid anhydride.

The present invention also provides a process for preparing a mixture containing a series of reaction products obtainable by releasing the C-terminal amino acids successively from a target peptide with use of chemical means, which is corresponding to the most characteristic step comprised in the above-mentioned method for analysis of C-terminal amino acid sequence of peptide according to the present invention; that is, the process of the present invention for preparing a mixture containing a series of reaction products obtainable by releasing the C-terminal amino acids successively from a peptide with use of chemical means is defined as a process for preparation of a mixture containing a series of reaction products obtainable by releasing the C-terminal amino acids successively from a target peptide with use of chemical means, wherein the process is conducted to prepare the mixture containing a series of reaction products obtainable by releasing the C-terminal amino acids successively from the peptide by the chemical means comprising steps of:

allowing an alkanoic acid anhydride and a perfluoroalkanoic acid both of vapor phase, which are supplied from a mixture of the alkanoic acid anhydride with a small amount of the perfluoroalkanoic acid added thereto, to act on a dried sample of the target peptide in a dry atmosphere at a temperature selected in a range of 15 to 60° C., and carrying out the release of the C-terminal amino acid in association with the process that at the C-terminus of the peptide, the formation of a 5-oxazolone structure represented by the following general formula (III):

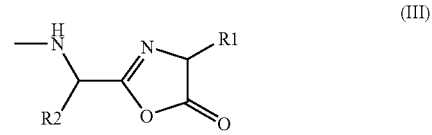

wherein R1 is a side chain of the C-terminal amino acid of the peptide, and R2 is a side chain of the amino acid residue positioned just before said C-terminal amino acid, is followed by the cleavage of the 5-oxazolone ring.

In addition, the present invention provides a kit for treatment that can be exclusively used for said treatment technique to successively release C-terminal amino acids according to the present invention; that is, the kit of the present invention used for the treatment of releasing the C-terminal amino acids successively is defined as a kit used for treatment of reaction to release the C-terminal amino acids successively from a target peptide by chemical means, wherein the kit for treatment of releasing the C-terminal amino acids successively is the kit being set up with a combination of:

as a liquid reagent for the reaction of releasing the C-terminal amino acids successively, at least a mixture obtained by a small amount of a perfluoroalkanoic acid to an alkanoic acid anhydride, or separately the alkanoic acid anhydride and the perfluoroalkanoic acid in combination for preparation of the mixture, a sample container for holding a sample of the target peptide to be treated therein, and a reactor vessel which is provided with a liquid reagent-holding system capable of reserving said liquid reagent therein and capable of maintaining such a state that said liquid reagent makes no direct contact with said peptide sample held in the sample container and which has capacity to accommodate said sample container inside.

BRIEF DESCRIPTION OF THE DRAWINGS

FIG. 1 is a diagram of process flow illustrating an example of the detailed procedures employed in the treatment to successively release C-terminal amino acids from a peptide, according to the present invention.

BEST MODE FOR CARRYING OUT THE INVENTION

Figure 2:
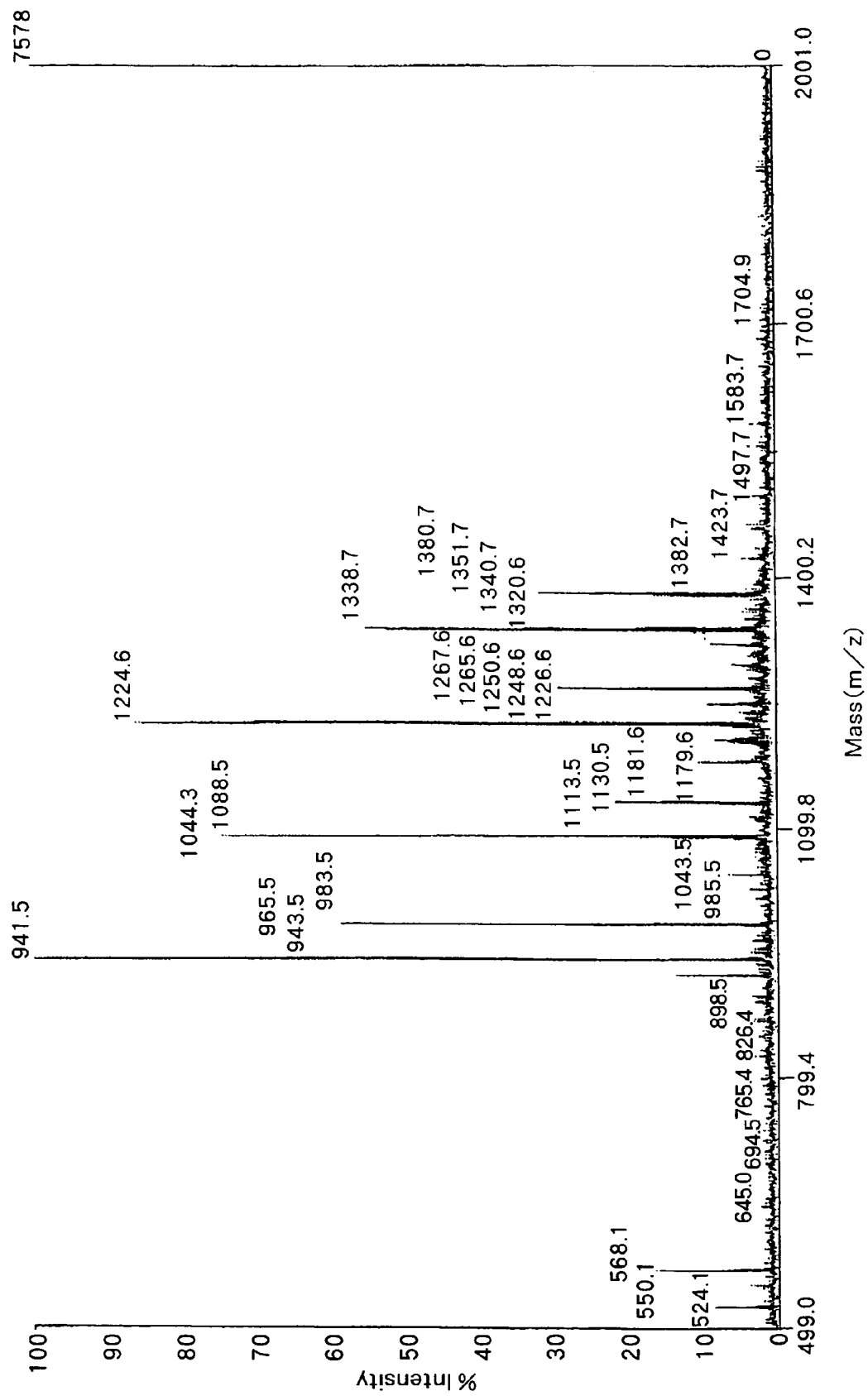
FIG. 2 shows an example of the spectra observed in mass spectrometric analysis of a mixture of reaction products, which are obtained by successively releasing the C-terminal amino acids from angiotensin I peptide according to the treatment method of the present invention for releasing C-terminal amino acids successively from the peptide.

The present invention is explained in more detail below.

The method for analysis of C-terminal amino acid sequence of peptide according to the present invention is basically utilizing such a technique comprising steps of releasing the C-terminal amino acids form the peptide successively to prepare a series of reaction products with truncated peptide chains relative to the peptide to be examined, and identifying the amino acids released therefrom, based on the differences between the series of the molecular weights for the reaction products and the molecular weight for the original peptide. In more particular, the method uses mass spectrometry as means for measuring the molecular weights of the series of reaction products and the molecular weight of the original peptide, and among others, there is preferably used a Time-of-Flight type mass spectrometer, for example, a MALDI-TOF-MS system, which is very suitable for a measurement conducted under such conditions as there takes place, in the step of ionization, no removal of fragments with atomic moieties from the amino acid residues composing the peptide.

Meanwhile, the most characteristic feature in the analysis method of the present invention is that in the step of releasing the C-terminal amino acids from the peptide successively, the method is using such a treatment comprising steps of allowing an alkanoic acid anhydride and a perfluoroalkanoic acid both of vapor phase, which are supplied from a mixture of the alkanoic acid anhydride with a small amount of the perfluoroalkanoic acid added thereto, to act on a dried sample of the target peptide in a dry atmosphere at a temperature selected in a range of 15 to 60° C., and carrying out the release of the C-terminal amino acid in association with the process that at the C-terminal of the peptide, the formation of a 5-oxazolone structure represented by the following general formula (III):

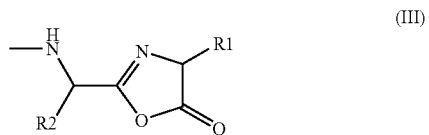

wherein R1 is a side chain of the C-terminal amino acid of the peptide, and R2 is a side chain of the amino acid residue positioned just before said C-terminal amino acid, is followed by the cleavage of the 5-oxazolone ring.

The reaction of the formation of said 5-oxazolone ring is expressed as a whole by the following reaction scheme (I):

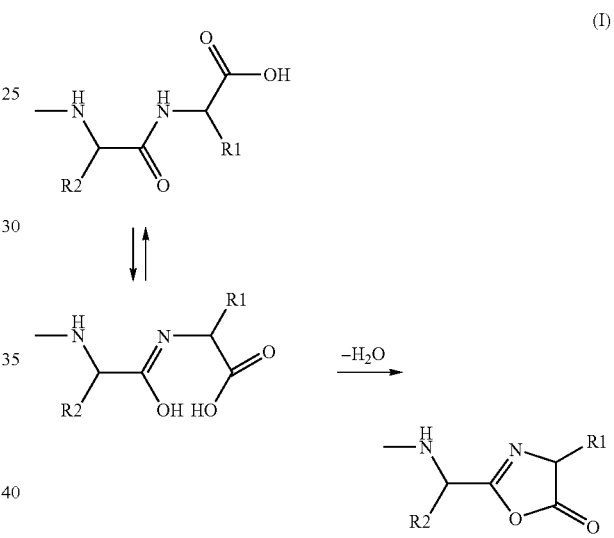

In particular, in the case of the process for selectively releasing C-terminal amino acid according to the present invention, at first, by choice of the step of allowing an alkanoic acid anhydride and a perfluoroalkanoic acid both of vapor phase and supplied from a mixture obtained by adding a small amount of a perfluoroalkanoic acid to an alkanoic acid anhydride, to act on a dried peptide in a dry atmosphere at a temperature of a range of 15 to 60° C., at the stage of the keto-enol tautomerism represented by the following reaction formula (Ia):

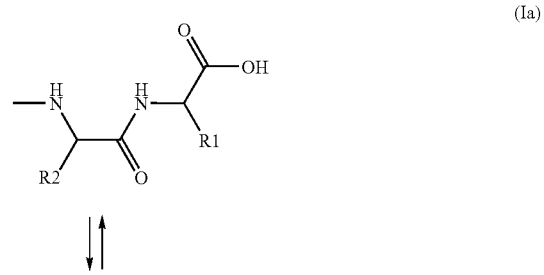

-continued

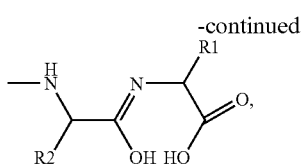

the ratio for staying in the enol state is heightened by allowing the perfluoroalkanoic acid of vapor phase to function as a proton donor toward the dried peptide.

Then, an intramolecular ester bond is formed between the hydroxy group exposed in the enol type and the C-terminal carboxy group to complete the 5-oxazolone ring-formation. On the other hand, in the case of the conventional method, the intramolecular ester bond is formed in a state in which a perfluoroalkanoic acid and water molecule, both of vapor phase, are generated from a high concentration aqueous solution of the perfluoroalkanoic acid by heating up to, for example, 90° C., and present together. It is expected that, in this esterification reaction as well, the perfluoroalkanoic acid of vapor phase maybe functions as a proton donor to induce the esterification reaction proceeding under an acid catalyst. However, since the reaction is carried out in a solvent-free solid phase, the reaction temperature is set high. Meanwhile, in the process for selectively releasing C-terminal amino acid according to the present invention, an alkanoic acid anhydride is used as a reagent for activation of C-terminal carboxy group; there occurs conversion into an asymmetric acid anhydride as illustrated by, for example, the following reaction formula (Ib);

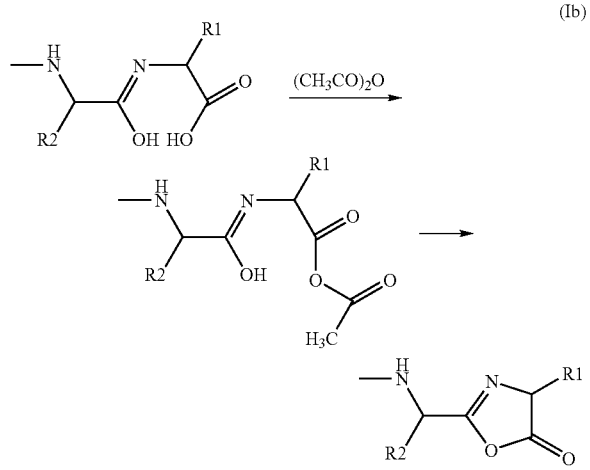

and thus the activated C-terminal carboxy group is involved in the reaction. As a result, such a reaction can proceed under a mild temperature condition and the reaction temperature can be selected in a range of 15 to 60° C. Incidentally, such a reaction temperature is selected preferably at around room temperature or in a temperature range slightly higher than room temperature, in more particular, more preferably in a range of 15 to 50° C.

Meanwhile, in the process for selectively releasing C-terminal amino acid according to the present invention, as for the perfluoroalkanoic acid used therein, its proton-donating ability is used, and thus a perfluoroalkanoic acid of which pKa is within the range of 0.3 to 2.5 is preferably used. In addition, since this perfluoroalkanoic acid needs to be supplied to a dried peptide in a vapor phase, it is preferred that the perfluoroalkanoic acid being be superior in volatility is selected so that a desired vapor pressure is obtained at said temperature selected in a range of 15 to 60° C. From this standpoint as well, a perfluoroalkanoic acid having 2 to 4 carbon atoms is more suitable, and a liner-chain perfluoroalkanoic acid having 2 to 4 carbon atoms is further more adapted. Specifically, use of trifluoroacetic acid ($CF_3COOH$), pentafluoropropanoic acid ($CF_3CF_2COOH$) or heptafluorobutanoic acid ($CF_3CF_2CF_2COOH$) is more desired.

On the other hand, the alkanoic acid anhydride used as an activation reagent is consumed with the progress of the reaction; therefore, it is desired to conduct the reaction while the vapor pressure of the alkanoic acid anhydride supplied in a vapor phase is maintained at a given level. Examples of the means adapted for the purpose include such a means that the reaction system is kept in a sealed state and thereby the vapor pressure of the alkanoic acid anhydride present in the system is stabilized. In more particular, exemplified is such a procedure in which a liquid mixture obtained by adding a small amount of a perfluoroalkanoic acid to an alkanoic acid anhydride is placed in a sealable reactor; the liquid mixture is once cooled to reduce its vapor pressure; in this state, the reactor inside is evacuated and then sealed off; the alkanoic acid anhydride is vaporized in the reactor by heating up to a reaction temperature. By employing such a procedure, there is another advantage that the leakage of water into the reactor can be prevented. Further, when evacuation is conducted so that no oxygen remains in the reaction system, for example, the sulfur present in methionine, which is included in the amino acid residues composing a peptide to be examined, can be prevented from oxidation by oxygen and consequent change of its formula weight. In the method of the present invention based on the measurement of molecular weights, such prevention of oxidation is more preferred for achieving a higher accuracy.

Incidentally, for example, when the peptide to be examined contains a plurality of cysteines which are forming an —S—S— bond of its oxidized type between a cysteine of adjacent peptide or forming a —S—S— bond within one peptide molecule, an ordinary reduction treatment is applied beforehand to eliminate such a linkage and thereby the peptide is converted into a peptide containing reduced forms of cysteines. Further, to the reduced form of cysteine present in a peptide is applied, for its protection, for example, carboxymethylation or pyridylethylation to the sulfanyl group (—SH) on its side chain.

Variety of alkanoic acid anhydrides, as long as they can produce an appropriate vapor pressure when heated to the temperature of reaction, is applicable as the alkanoic acid anhydride used therein. Meanwhile, there is preferred an alkanoic acid anhydride which gives a sufficient vapor pressure when the reaction temperature is selected in the above-mentioned preferable range, for example, of 15 to 50° C. Therefore, a symmetric anhydride of an alkanoic acid having 2 to 4 carbon atoms is used preferably. Among others, as the symmetric acid anhydride, a symmetric anhydride of a linear-chain alkanoic acid anhydride having 2 to 4 carbon atoms is used more preferably, and in particular, a symmetric anhydride of a linear-chain alkanoic acid having 2 carbon atoms, i.e. acetic acid is used appropriately. Since such an alkanoic acid anhydride is used for the activation of C-terminal carboxy group, the anhydride is preferred to give minimum steric hindrance, and the above-mentioned acetic acid, etc. are very suitable in this respect as well.

In said reaction of releasing amino acids, the alkanoic acid anhydride and the perfluoroalkanoic acid are allowed to act on a dried peptide in respective vapor states. The reaction is conducted in a dry atmosphere in order to avoid the hydrolysis of once-formed 5-oxazolone ring by the water incoming from outside of the system and its reversion to original structure. In this view, the reaction is desired to be carried out generally in a sealed reactor. Incidentally, the mixture of the alkanoic acid anhydride and perfluoroalkanoic acid, initially fed into the reactor is, at room temperature, a liquid mixture wherein the alkanoic acid anhydride and perfluoroalkanoic acid are mixed uniformly. In this mixture containing the alkanoic acid anhydride with a small amount of the perfluoroalkanoic acid added thereto, the perfluoroalkanoic acid functioning as a catalyst is not consumed during the reaction in principle and therefore its content can be a small amount. More specifically explaining, the vapor of perfluoroalkanoic acid present in the vapor phase, as compared with the vapor of alkanoic acid anhydride co-existing, can be in a relatively low concentration. In other words, depending upon the kinds of the alkanoic acid anhydride and perfluoroalkanoic acid used, for instance, on the respective saturated vapor pressures thereof at the reaction temperature, there is appropriately selected a liquid mixture having a mixing ratio which can achieve an intended partial pressure ratio (a concentration ratio in vapor phase). The content of perfluoroalkanoic acid, in the mixture containing the alkanoic acid anhydride with a small amount of the perfluoroalkanoic acid added thereto, is desired to be selected, for example, in a range of 1 to 20% by volume, preferably in a range of 3 to 10% volume relative to the total volume of the alkanoic acid anhydride and the perfluoroalkanoic acid.

In the process for selectively releasing C-terminal amino acid according to the present invention, it is concluded that, from the once-formed 5-oxazolone ring, the separation of the C-terminal amino acid and the formation of the reaction intermediate for the next-stage may proceed, for instance, via such reaction as shown by the following reaction formula (II'):

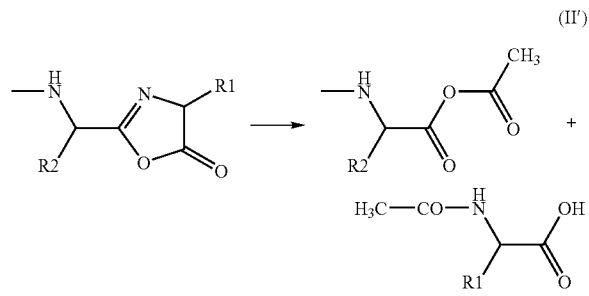

as a result, successive release of C-terminal amino acids is advanced in such way. Therefore, the reaction products obtained after the completion of such reactions are the mixture comprising, in addition to those having a carboxy group exposed at the C-terminal, such as shown in the above reaction formula (II), an intermediate product having the 5-oxazolone ring structure and a form of reaction intermediate in which its C-terminal is converted into the form of asymmetric acid anhydride.

The successive reaction used in the treatment step of releasing C-terminal amino acid selectively is constructed at least with two-stage elementary reactions, i.e. a stage of formation of 5-oxazolone ring structure as illustrated by the reaction formula (Ib) and a stage of separation of C-terminal amino acid by the cleavage of 5-oxazolone ring structure, as illustrated by the reaction formula (II'). Therefore, the overall reaction rate depends upon the reaction rates of the two stages, but depends mainly upon the partial pressures (concentrations in vapor phase) of the alkanoic acid anhydride and perfluoroalkanoic acid used therefor as well as the reaction temperature therein. In addition, as a series of reaction products are formed by successive reactions, the maximum length of C-terminal amino acid sequence removed, which can be attained in the series of reaction products obtained, becomes longer as the treatment duration becomes longer. Hence, the treatment duration for the treatment step of selectively releasing C-terminal amino acid in such a successive manner needs to be appropriately chosen depending mainly upon the partial pressures (concentrations in vapor phase) of the alkanoic acid anhydride and perfluoroalkanoic acid and the reaction temperature employed therefor and also in view of the intended length of the C-terminal amino acid sequence to be analyzed.

It is possible to arrange additional treatment for hydrolysis at the end in order to convert the forms of reaction intermediate having no carboxy group exposed at the C-terminal, such as illustrated in the above reaction formula (II'), formed during the treatment step of selectively releasing C-terminal amino acid in such a successive manner, into a form having a exposed carboxy group exposed at the C-terminal. Hence, in the process of the present invention for releasing C-terminal amino acids selectively, it is preferred to provide, in addition to said step of the treatment with use of a mixture obtained by adding a small amount of a perfluoroalkanoic acid to an alkanoic acid anhydride, the process with additional steps for hydrolysis treatment comprising steps of:

applying, to the mixture containing a series of reaction products, which is obtained in said step of releasing the C-terminal amino acids successively, a post-treatment of removing the residual alkanoic acid anhydride and perfluoroalkanoic acid therein in a dry state, then, feeding a basic, nitrogen-containing aromatic cyclic compound or a tertiary amine compound and water molecule both of vapor phase supplied by using an aqueous solution in which the basic, nitrogen-containing aromatic cyclic compound or tertiary amine compound is dissolved, allowing the water molecule to act on the reaction products of peptide in the presence of said basic, nitrogen-containing organic compound, and after said treatment for hydrolysis, re-drying post-treatment which is conducted by removing the basic, nitrogen-containing organic compound and water molecule both remaining in the mixture containing a series of the reaction products, followed by drying. By application of this post-treatment, the reaction products come to take forms having a carboxy group exposed at the C-terminal. These forms give major peaks in the analysis by mass spectrometry conducted thereafter, which makes easier the operation for identification of peaks with the molecular weights corresponding to a series of reaction products in the light of the peak intensities thereof.

The basic, nitrogen-containing aromatic cyclic compound or tertiary amine compound both of vapor phase has no ability to react with, for example, products remaining such a form in which its C-terminal has been turned into an asymmetric acid anhydride or to form any amide bond therewith; and further, the basic, nitrogen-containing aromatic cyclic compound or tertiary amine can be made into a uniform solution when preparing an aqueous solution thereof; which features are preferably fit to use for the treatment of hydrolysis. As the basic, nitrogen-containing aromatic cyclic compound which can be used, there is preferred a monocyclic nitrogen-containing aromatic compound which can give an appropriate vapor pressure, and, for example, pyridine can be more suitably used. As the tertiary amine compound which can be used, there is preferred one having the same weak basicity as shown by pyridine and, for instance, such as DMAE [(CH$_3$)$_2$N—CH$_2$CH$_2$OH] can be suitably used. When, for example, pyridine is used, the pyridine content is preferably selected in a range of 5 to 15% by volume, in more particular at 10% by volume relative to the whole volume of the aqueous solution thereof. When (dimethylamino) ethanol (DMAE) is used, the DMAE content is preferably selected in a range of 1 to 20% by volume, in more particular at 10% by volume relative to the whole volume of the aqueous solution thereof.

The monocyclic nitrogen-containing aromatic compound or tertiary amine compound is allowed to act on a dried mixed sample containing the reaction products, in the vapor state together with water molecule. In this post-treatment, the reaction as well is desired to be conducted in a sealed reactor. In said post-treatment, since water molecule is used, its vapor pressure needs to be set at a certain level or higher. Therefore, the treatment temperature is desirably chosen, for example, from a temperature of 60° C. or more but, when the mechanical strength of the reactor is taken into consideration, in a range of 100° C. or lower. In order to complete the treatment for hydrolysis quickly, such a temperature of 100° C. or slightly lower is desired to be selected.

Moreover, in the process for selectively releasing C-terminal amino acid according to the present invention, in addition to the step of the treatment using a mixture obtained by adding a small amount of a perfluoroalkanoic acid to an alkanoic acid anhydride, the process may be provided, prior to said step of releasing the C-terminal amino acids successively, with a step for a pre-treatment of applying, to the N-terminal amino group of the peptide to be examined, N-acylation protection in advance with use of an acyl group derived from the alkanoic acid constituting said alkanoic acid anhydride. Specifically explaining, in said step of the treatment using a mixture obtained by adding a small amount of a perfluoroalkanoic acid to an alkanoic acid anhydride, a reaction intermediate wherein the C-terminal carboxy group of peptide is activated, is presumed to be formed. When this reaction intermediate would react with the N-terminal amino group of an adjacent peptide to form an amide bond therewith, no intended reaction product with truncated peptide chain is obtained. Since the reaction per se is carried out in a solid phase, frequency of such accidental side reaction is not so high. However, N-acylation is desirably applied beforehand to protection against the side reaction.

In addition, during said treatment using a mixture obtained by adding a small amount of a perfluoroalkanoic acid to an alkanoic acid anhydride, the N-terminal amino group of peptide ordinarily undergoes N-acylation by the alkanoic acid anhydride, and accordingly N-acylation protection takes place in the reaction system; nevertheless, it is more desired to conduct the pretreatment aiming at N-acylation protection.

The pretreatment step of applying N-acylation protection to the N-terminal amino group may be conducted by employing technique where the N-acylation for amino groups in the peptide is effected by allowing an alkanoic acid anhydride and an alkanoic acid both of vapor phase, which are supplied from a mixture obtained by adding a small amount of the alkanoic acid to the alkanoic acid anhydride, to act on a dried sample of the peptide to be examined in a dry atmosphere at a temperature selected in a range of 10 to 60° C. In such a case, it is preferred that the alkanoic acid anhydride used in the pretreatment step of applying N-acylation protection to the N-terminal and as the alkanoic acid anhydride used in the step conducted thereafter of releasing the C-terminal amino acids successively, used is the same alkanoic acid anhydride. Specifically explaining, in the pretreatment reaction for applying N-acylation protection to the N-terminal amino group, the reaction is allowed to proceed by supplying, to the dried peptide sample, the alkanoic acid anhydride and alkanoic acid both in a vapor state; therefore, in order to obtain appropriate vapor pressures thereof, there can be suitably used the same alkanoic acid anhydride as the alkanoic acid anhydride used in the step conducted thereafter, of releasing the C-terminal amino acids successively. In addition, since the reactivity of the alkanoic acid anhydride is too low to cause undesired side reactions such as peptide cleavage, in a dry atmosphere at a temperature of a range of 10 to 60° C. and further since the alkanoic acid to be used together is strikingly inferior in acid catalytic activity to perfluoroalkanoic acid, the combination can provide N-acylation protection to N-terminal amino group in the pretreatment, with much less possibility to invite undesired side reactions.

Additionally, in the step of N-acylation protection to the N-terminal amino group of peptide, N-acylation protection proceeds simultaneously also to the ε-amino group on the side chain of the lysine residue present in the peptide. Furthermore, O-acylation proceeds also to the hydroxyl groups on the side chain of the serine and threonine resides present in the peptide, and thereby protection thereof is made. Besides, the phenolic hydroxyl group on the side chain of the tyrosine residue present in the peptide also undergoes partially O-acylation although its reactivity is varied. As a result of the pretreatment step wherein a plurality of these acylation protections take place as well, the amino group on the side chain of lysine residue and the hydroxyl group on the side chain of serine and threonine residues are all modified with the protection group, and are no longer able to take part in undesired side reactions. It is generally preferred from this standpoint as well that the pretreatment step of application of the N-acylation protection to the N-terminal amino group of peptide is conducted in advance.

Incidentally, in the combination use of the alkanoic acid anhydride and alkanoic acid in the pretreatment step, there is substantially no fear of undesired side reactions, for example, such as cleavage in the middle of peptide. However, the pretreatment temperature is preferred to be selected in a range of 10 to 60° C., more preferably at around room temperature or a temperature range slightly higher than room temperature, and in more particular in a range of 15 to 50° C. On the other hand, the content of the alkanoic acid in the mixture obtained by adding a small amount of the alkanoic acid to the alkanoic acid anhydride is preferred to be selected in a range of 2 to 10% by volume, specifically at 5% by volume relative to the total volume of the alkanoic acid anhydride and alkanoic acid.

Besides, the procedure for reaction in the pretreatment step is preferably conducted in very similar manner to the above-mentioned procedure for the step of selectively releasing C-terminal amino acids. That is, the above-mentioned procedure for operation and conditions suitable to the step for selectively releasing C-terminal amino acids are also adapted to said reaction step in the pretreatment step.

Incidentally, the rate of N-acylation reaction in the pretreatment step depends upon the partial pressures (concentrations in vapor phase) of the alkanoic acid anhydride and alkanoic acid used as well as the reaction temperature; therefore, the reaction time of the pretreatment step is desired to be selected appropriately depending mainly upon the reaction temperature. When the reaction temperature is selected at, for example, 50° C., the reaction time is selected to be within one hour, for example, for 30 minutes, whereby the N-acylation to the N-terminal amino group of peptide can be completed. In such a case, addition of pyridine of catalytic amount, for example, 0.1 to 1.0% by volume relative to the total volume of the alkanoic acid anhydride and alkanoic acid is more preferred in order to enhance the acylation reaction with use of the alkanoic acid anhydride and the alkanoic acid. Since this pyridine base functions as a proton receptor, for example, removal of protons to be eliminated in association with the acylation to amino group is made more swiftly.

Further preferably, the process for selectively releasing C-terminal amino acids according to the present invention is carried out in such a mode in which the pretreatment step, the reaction step of selectively releasing C-terminal amino acids and the post-treatment step are all comprised. An example of such a flow pattern of steps is illustrated in FIG. 1. A drying-up operation is conducted in said flow when each step has been completed, so that the reagents used in each step do not remain in the peptide sample. This drying-up operation is generally conducted by vacuum distillation, and thereby the C-terminal amino acids released that are by-products in said reaction can be removed as well, in some cases. The flow pattern of steps of FIG. 1 illustrates an example wherein acetic anhydride of high availability in a very high purity is utilized as the alkanoic acid anhydride used therein.

On the other hand, in the flow pattern of steps illustrated in FIG. 1, as for the treatment duration in the reaction step of selectively releasing C-terminal amino acids, illustrated is a range of treatment time which is selected depending upon the proportions of the acetic anhydride and fluoroalkanoic acid used and the treatment temperature employed, for model case where the length of amino acids of the C-terminal amino acid sequence to be truncated in said step are intended to be ten odd amino acids as maximum case and 3 amino acids as minimum case. In general, when the proportion of the fluoroalkanoic acid is larger and the treatment temperature is higher, the reaction rate is higher, and thereby it is possible to prepare a series of reaction products that have attained the maximum of truncated length of amino acid sequence, which is set as the goal, in shorter treatment duration.

Furthermore, in the pretreatment step, N-acetylation to N-terminal amino group of peptide is carried out by using acetic anhydride and acetic acid both of vapor phase. Even in the case of such combination of acetic anhydride and acetic acid, there is, in some cases, a fear, maybe very small, that the activation reaction to C-terminal carboxy group expressed by the above-shown reaction formula (Ia) and the side reaction caused thereby take place. In order to suppress such side reaction, a small amount of pyridine vapor can be allowed to co-exist to form a weak addition salt between the pyridine base and the C-terminal carboxy group of peptide, which may provide protection effect against the occurrence of the undesired side reaction. Such protection of addition salt formation type undergoes easy deprotection by conducting a drying-up operation upon completion of the pretreatment step to distil off the pyridine base under vacuum, and no problem occurs in the next reaction step of selectively releasing C-terminal amino acids. From these standpoints, it is preferred to add, for the protection of addition salt formation type, a small amount of a nitrogen-containing heterocyclic aromatic compound which can be easily distilled off under reduced pressure and has a weak basicity, such as pyridine. Further, since the protection of addition salt formation type possesses protective function also for the carboxy group on the side chain of amino acid, it can effectively prevent even the undesired side reaction that is originated from the carboxy group on the side chain of amino acid coincidently.

In the method of the present invention for analysis of C-terminal amino acid sequence of peptide, the molecular weights of the series of reaction products prepared by successively releasing C-terminal amino acids and the molecular weight of the original peptide are determined by consulting measured data by mass spectrometry and there are identified amino acids corresponding to the differences in the molecular weights thereof. Therefore, it is generally desired that the original peptide remains in the mixture subjected to the measurement by mass spectrometry, in such an amount as to enable the determination of its molecular weight.

Specifically explaining, the method of the present invention for analysis of the C-terminal amino acid sequence of peptide may be applied to such a case where maximum length analyzed for the C-terminal amino acid sequence is as long as ten and odd amino acids. With respect to the contents of the series of reaction products of which sorts reach, as maximum case, correspondingly into the number of ten and odd, the content of the minimum content reaction product is desired at least to be not smaller than about $1/10$ of the content of the maximum content reaction product. In addition, the remaining amount of the original peptide as well is desired at least to be not smaller than about $1/10$ of the content of the maximum content reaction product. Meanwhile, the required information of C-terminal amino acid sequence is within 10 amino acids in many cases and, when selecting the treatment time in which about 10 amino acids can be released, the above-mentioned requirements regarding the contents can be satisfied.

Meanwhile, mass spectrometry is used for the measurement of molecular weight. The measurement is more suitably conducted using a mass spectrometer equipped with such means for ionization that is well operated under such conditions as to suppress the fragmentation resulting in detachment of part of atomic moieties from the amino acid residues comprising the peptide, in the ionization step therein. Furthermore, as a peptide or the like has a high molecular weight, it is preferred to use a Time-of-Flight type mass spectrometer, for instance, such as MALDI-TOF-MS system, which is suitable for measurement in such a high molecular weight range. However, even when such a type of mass spectrometer is used, there is an upper limit as to the molecular weight allowing for effective ionization, and therefore it is desired that the maximum amino acids of a peptide that is possibly subjected to measurement does not exceed the limit of 20 to 30 amino acids. In addition, amino acids corresponding are identified based on the measured differences in molecular weight; therefore, in order to distinguish two amino acid residues giving a formula weight difference of 1, for instance such as Asn vs Asp, or Gln vs Glu, from each other at a high precision, the molecular weight of the longest peptide, i.e. the peptide with no release of C-terminal amino acid therefrom that is used as a datum point, is preferably in a range of no more than 3,000, more preferably in a range of no more than 2,000. When reduced to amino acids, it is preferred that its length is 30 amino acids at longest, more preferably in a range of no more than 20 amino acids.

When the method of the present invention for analysis of C-terminal amino acid sequence of peptide is applied to a peptide having length of amino acids far more than the limit mentioned above, e.g. a protein, it is desired to conduct, prior to carrying out mass spectrometry, treatment for specific cleavage of the peptide is carried out by using, for example, a protease having a specificity for the cleavage site of amino acid sequence, to allow the C-terminal peptide fragment obtained to have length of amino acids within the above-mentioned range. That is, when the same treatment for site-specific cleavage is applied to both the original peptide and a series of the reaction products prepared therefrom, the resulting C-terminal peptide fragments are a series of peptide fragments which has the same N-terminal amino acid but difference in C-terminal amino acid thereof. By using a mixture comprising such series of peptide fragments to identify their molecular weights by means of mass spectrometry, the method of the present invention for analysis of C-terminal amino acid sequence of peptide can be utilized.

However, when the present analysis method is applied to a long peptide such as a protein, in such a case that, in the long peptide, —S—S— bond between cysteine residues is formed owing to protein folding, it is necessary to beforehand reduce the —S—S— bond to eliminate the bridging between cysteine residues; further, the reduced form of cysteine is modified by carboxymethylation or the like to protect the sulfanyl group (—SH) on the side chain. Also, in the region constituting a secondary structure such as α-helix in association with the protein folding, the carbonyl group (C═O) and imino group (—NH—) of amino acid residue constituting the amide bond are in the state forming intramolecular hydrogen bond. When being held in such state forming the intramolecular hydrogen bond, the progress of the reaction used in the present invention may be suppressed. In view of this, it is desired that peptide is in advance treated to convert into the state where no secondary structure is constructed at least in the C-terminal portion thereof, for example, being treated for de-folding, and thereafter, drying of such peptide sample is conducted, and then the above-mentioned chemical treatment is applied thereto. When peptide is in the shape being treated for de-folding, for example, in such a case that after a series steps of chemical treatments have been completed, site-specific cleavage of the peptide using a protease or the like is needed prior to step of analysis in mass spectrometry, it has such an advantage that the C-terminal peptide fragments obtained therein are generally easy to separate.

In the method of the present invention for analysis of C-terminal amino acid sequence of peptide, the amino acids released successively are identified based on the differences in molecular weight. Therefore, distinction between leucine (Leu) residue and isoleucine (Ile) residue both having the same formula weight is impossible in principle, which is the same as in the conventional method for analysis of C-terminal amino acid sequence using mass spectrometry. On the other hand, in the reaction for releasing C-terminal amino acid, conversion of amide bond into enol from and subsequent formation of 5-oxazolone ring structure are essential as shown in the reaction formula (Ib), and thus no further reaction for releasing proceeds when cyclic amino acid proline (Pro), in which any imino group (—NH—) forming amide bond together with carbonyl group (C═O) is not present, has come to be the C-terminal amino acid. In other words, by confirming that there occurs no further elimination of C-terminal amino acid even when treatment duration is prolonged, it is possible to predict that the amino acid residue that is main factor for such arrest is cyclic amino acid proline (Pro).

The process of the present invention for preparing a mixture comprising a series of reaction products obtainable by releasing the C-terminal amino acids successively from the peptide with use of chemical means corresponds to the technique used in the reaction step of releasing C-terminal amino acid selectively for the method of the present invention for analysis of C-terminal amino acid sequence of peptide explained above. Therefore, the preferred mode for carrying out the process is the same as described previously. This technique can be applied not only for a linear peptide to prepare a sample used for determination of C-terminal amino acid sequence thereof but also for a cyclic peptide to prepare a sample used for determining amino acid sequence thereof, wherein by ring-opening, the cyclic peptide is in advance converted into form of linear peptide, which is subjected to determination of its C-terminal amino acid sequence. Specifically explaining, various microorganisms for example, produce cyclic peptide type compounds having biological activities, and said technique can be applied for preparation of a sample for determination of the structures of such compounds.

Even in said process of the present invention for preparing a mixture containing a series of reaction products obtainable by releasing the C-terminal amino acids successively from the peptide with use of chemical means, for example, when there occur N,O-acyl rearrangement for the hydroxy groups present on the serine residue [—NH—CH(CH$_2$OH)—CO—] and threonine residue [—NH—CH(CH(CH$_3$)OH)—CO—] in the peptide, which subsequently results in branching, the ester bond therein, as compared with amide bond, undergoes cleavage more easily. However, owing to the action of alkanoic acid anhydride and perfluoroalkanoic acid both of vapor phase, O-alkanoylation to the hydroxy group on their side chain proceeds preferentially, which attains effectively competitive inhibition against the N,O-acyl rearrangement. Incidentally, when the post-treatment step is carried out, the ester bond to alcoholic hydroxy group, as compared with the ester bond to phenolic hydroxy group, undergoes hydrolysis more quickly, and accordingly there remain, at high selectivities in the reaction products obtained finally, only N-alkanoylation to N-terminal amino group, N-alkanoylation to the amino group on the ε-position of lysine residue [—NH—CH(CH$_2$CH$_2$CH$_2$CH$_2$NH$_2$)—CO—] and, in some cases, also O-alkanoylation to the phenolic hydroxy group of tyrosine residue [—NH—CH(CH$_2$—C$_6$H$_4$—OH)—CO—].

For example, when numbers of acetylated forms of serine residue and threonine residue are included in the reaction products obtained finally, the molecular weight differences between such multi-acetylated product and deacetylated product are aligned in the integral times of formula weight 42, specifically 84, 126 and 168 are close to the formula weight 87 of serine residue [—NH—CH(CH$_2$OH)—CO—], the formula weight 128 of glutamine residue [—NH—CH(CH$_2$CH$_2$—CONH$_2$)—CO—] or the formula weight 129 of glutamic acid residue [—NH—CH(CH$_2$CH$_2$—COOH)—CO—] and the formula weight 170 of N-acetyllysine residue [—NH—CH(CH$_2$CH$_2$CH$_2$CH$_2$NH—COCH$_3$)—CO—], respectively. Therefore, there is some fear that the peak for the multi-acetylated products may be mistaken as main peaks, and the deacetylated products may be mis-assigned as derived products therefrom with the release of such an amino acid. However, actual measurement is made in such an analytical precision that the distinction between glutamine residue and glutamic acid residue, of which the formula weights differ only 1, is possible; since the formula weight difference related to the difference in number of remaining acetyl groups differs from the formula weight of amino acid residue showing a similar formula at least with the Formula weight difference of 2 to 3; the possibility of such mis-assignment mentioned above is not high in many cases. However, it is preferred to carry out the post-treatment to eliminate such undesired remains of the alkanoyl groups.

The kit of the present invention used for treatment to release the C-terminal amino acids successively is a kit being set up with a combination of a reactor vessel and a set of reagents usable under the reaction conditions suitable for said reactor vessel, which is applicable to the reactions used exclusively in the aforementioned process of the present invention for preparing a mixture containing a series of reaction products obtainable by releasing the C-terminal amino acids successively from a peptide with use of chemical means. The set of reagents for said reactions include, as a liquid reagent for the reaction of releasing the C-terminal amino acids successively, at least a mixture obtained by a small amount of a perfluoroalkanoic acid to an alkanoic acid anhydride, or separately the alkanoic acid anhydride and the perfluoroalkanoic acid in combination for preparation of the mixture. Since the same type of reactor can be used also in the pretreatment step as well as the post-treatment step explained above, the kit may be set up to further comprise the reagents used in the pretreatment step and the post-treatment step therein. It is preferable for the kit to select the compositions and use amounts of these reagents being adapted to the reaction conditions explained above.

With respect to the sample container for holding a sample of target peptide to be treated, since a solution containing the peptide sample is fed therein, and then treatment for drying up is conducted, and subjected thereafter to an intended treatment(s), the sample container can be formed in shape of a micro vial type used in treatment of freeze-drying or of a multi-well plate type used in simultaneous handling of a plurality of peptide samples.

The reactor vessel is provided with a liquid reagent-holding system that is capable of reserving the liquid reagent for said reaction or each of the liquid reagents combined in the component kit thereof respectively, capable of feeding the liquid reagents for said reactions at given rates to the peptide sample held in said sample container, and capable of maintaining such a state that their direct contact with each other is avoided, and the reactor vessel has capacity to accommodate said sample container inside. Preferably, the reactor vessel is designed in such a form that the inside can be evacuated, the liquid reagents remaining therein after the completion of the reaction can be distilled off under reduced pressure, and the structure can be made gas-tight during the reaction In addition, the reactor vessel is required to be made of such a material that, when the vapor of the reagent is generated in the reactor vessel, no reaction takes place between the reagent and the wall of the vessel. Therefore, there is suitably used such a vessel formed by using glass material that is widely used for reactor in chemical reactions. For the cocks used in a sealed-state operation, cocks made of such a material as Teflon® or the like is used suitably.

EXAMPLES

The present invention is described specifically below by way of Examples. These Examples are examples of the best mode for carrying out the present invention; however, the present invention is in no way restricted by such specific embodiments illustrated thereby.

Example 1

In order to verify the usefulness of the method for analysis of the C-terminal amino acid sequence of peptide according to the present invention, analysis of C-terminal amino acid sequence was conducted for human angiotensin I, which is a peptide comprising 10 amino acids.

With respect to human angiotensin I, which is the peptide to be examined in the present Example, its amino acid sequence is already known to be Asp-Arg-Val-Tyr-Ile-His-Pro-Phe-His-Leu. Using this peptide, the precision of identification for the C-terminal amino acid sequence analyzed by means of the analysis method according to the present invention was verified.

(Pretreatment Operation)

First, a peptide solution containing 10 pmol of commercially available human angiotensin I is fed into a micro vial and subjected to a freeze-drying treatment. The vial containing the dried peptide sample was set in a glass-made reactor of air-tight test tube type with fitting stopper, having an evacuation port equipped with a Teflon-made cock valve for sealing. Separately, a given amount of the following liquid reagent is placed in the glass-made reactor.

As the reagent for pretreatment, there is used 300 µl of acetic anhydride containing 5% by volume of acetic acid. After the vial containing the dried peptide sample has been set up in the glass-made reactor, the reactor inside is evacuated under cooling condition and then sealed in an air-tight state.

The whole reactor of air-tight state is kept at 50° C. for 1 hour to allow acetic anhydride and acetic acid both of vapor phase, supplied from the liquid reagent in the reactor, to act on the dried peptide sample. By allowing acetic anhydride in the co-presence of acetic acid as an acylation reagent to act on the dried peptide sample, selective acetylation to the N-terminal amino group of the peptide proceeds. As a result, the peptide is converted into N-acetylated human angiotensin I. After such pretreatment has been completed, the unreacted acetic anhydride, acetic acid, etc. remaining in the reactor is distilled off under reduced pressure and the N-acetylated human angiotensin I obtained is dried.

(Operation for Releasing C-Terminal Amino Acid)

Next, in a state that the vial holding the dried sample of N-acetylated human angiotensin I prepared is set similarly in the glass-made reactor of air-tight test tube type with fitting stopper, a given amount of the following liquid reagent is placed anew in the glass-made reactor.

As a liquid reagent for the reaction of selectively releasing C-terminal amino acid, 300 µl of acetic anhydride containing 5% by volume of trifluoroacetic acid is used. After the vial containing the dried sample has been set up-in the glass-made reactor, the reactor inside is evacuated under cooling condition and then sealed in an air-tight state.

The whole reactor of air-tight state is kept at 40° C. for 16 hours to allow acetic anhydride and trifluoroacetic acid both of vapor phase, supplied from the liquid reagent in the reactor, to act on the dried sample. In this case, since acetic anhydride functions as an acylation reagent in the co-presence of trifluoroacetic acid, O-acetylation proceeds to the phenolic hydroxy group on the side chain of tyrosine (Tyr). Meanwhile, at the C-terminal of peptide, there proceed keto-enol tautomerism represented by the following reaction formula (Ia), promoted by trifluoroacetic acid functioning as a proton donor:

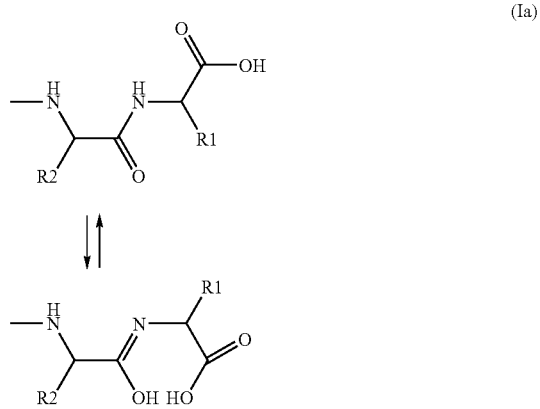

(Ia)

and conversion into asymmetric acid anhydride and formation of cyclic ester, which occur by the action of acetic anhydride on C-terminal carboxy group and are represented by the following reaction formula (Ib);

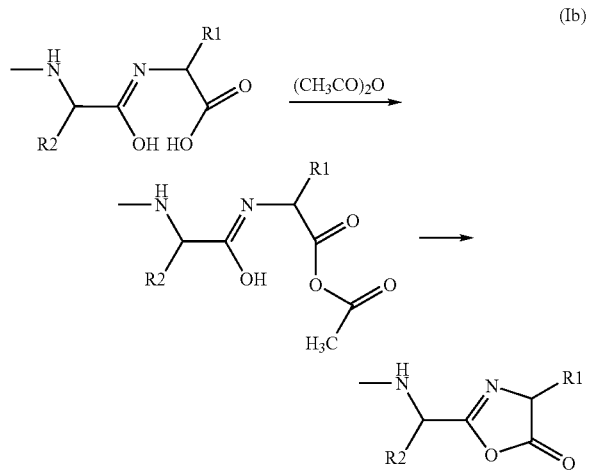

(Ib)

and whereby the C-terminal is once converted into a 5-oxazolone structure. Further, the oxazolone ring is cleaved with the help of acetic acid (CH₃COOH) by-produced in the above reaction or of trifluoroacetic acid which is co-present, and the C-terminal amino acid is eliminated as N-acylated amino acid [Ac—NH—CH(R1)—COOH] and from the amino acid residue [—NH—CH(R2)—CO—] positioned just before the C-terminal acid, its terminal carboxy group comes to be exposed newly. Furthermore, a reaction to the next stage proceeds and the next amino acid ahead that has been newly exposed at C-terminal is converted into a 5-oxazolone structure as well.

Thus, leucine (Leu), histidine (His) and phenylalanine (Phe) are successively released from the C-terminal of human angiotensin I to reach reaction product in which proline (Pro) is exposed at the C-terminal. Proline contains amino nitrogen in the ring structure; therefore, when a peptide bond is formed thereto, there occurs no keto-enol tautomerism represented by the above-shown reaction formula (Ia). Accordingly, the reaction can never progress in further conversion into a 5-oxazolone structure represented by the reaction formula (Ib). As a result, under the conditions of allowing a vapor phase acetic anhydride to act in the co-presence of trifluoroacetic acid, there is no selective release of proline (Pro) positioned at the C-terminal That is, the reaction products obtained in the present Example are only three kinds of truncated peptides in which leucine (Leu), histidine (HiS) and phenylalanine (Phe) have been released successively. On the other hand, with respect to the C-terminals of said three kinds of truncated peptides, they are in the mixture state including those staying in the 5-oxazolone structure, or being advanced even in conversion into an asymmetric acid anhydride therefrom, other than those being converted into carboxy group.

After the completion of the treatment for selective releasing C-terminal amino acids, the unreacted acetic anhydride, trifluoroacetic acid, etc. remaining in the reactor are distilled off under reduced pressure and a mixture of the residual N-acetylated human angiotensin I and the reaction products obtained is dried.

(Post-Treatment Operation)

Next, in a state that the vial holding the dried sample of a mixture of N-acetylated human angiotensin I and the obtained reaction products is set similarly in the glass-made reactor of air-tight test tube type with fitting stopper, a given amount of the following liquid reagent is placed anew in the glass-made reactor.

As in the above mixture, the C-terminals of reaction products of peptide are in the mixture state including those staying in the 5-oxazolone structure or being advanced even in conversion into an asymmetric acid anhydride therefrom, other than those being converted into carboxy group, the post-treatment is a treatment mainly aiming to convert them into the state where the C-terminals of the peptides all turned carboxy groups by applying treatment for hydrolysis to them. That is, an aqueous solution of a basic, nitrogen-containing organic compound is used as a liquid reagent for post-treatment, and the basic, nitrogen-containing organic compound and water molecule both of vapor phase, generated from the solution are allowed to act on said mixture which is dried beforehand. In the present Example, 300 μl of an aqueous solution holding 10% by volume of pyridine therein is used as the liquid reagent for the post-treatment of hydrolysis; and after the vial containing the dried sample has been set in the glass-made reactor, the inside of the reacter is evacuated under cooling condition and then sealed in an air-tight state.

The whole reactor of air-tight state is heated at 100° C. for 30 minutes to allow the vapor-phase pyridine and water molecule, supplied from the liquid reagent in the reactor, to act on the dried sample. The asymmetric acid anhydride and the 5-oxazolone structure undergo hydrolysis by the action of water molecule in the co-presence of pyridine base, whereby they are converted into a form having a carboxy group at the C-terminal. Hydrolysis of ester bond proceeds also to the O-acetylated phenolic hydroxy group on the side chain of tyrosine (Tyr), whereby deacetylation (deprotection) thereof is made partially. Meanwhile, in N-acetylation, i.e. the acetyl group being substituted on N-terminal amino group, no hydrolysis of amide bond takes place under the above-mentioned conditions. Therefore, the reaction products obtained after the post-treatment are N-acetylated products in which the N-terminal of peptide is modified with the acetyl group. Consequently, in the reaction products, the N-terminal of peptide is modified with the acetyl group and the C-terminal has an exposed carboxy group; but they stay still in such state that those containing O-acetylation on the side chain of the tyrosine (Tyr) are partially remained.

After the post-treatment has been completed, the residual water molecule, pyridine, etc. in the reactor are distilled off under reduced pressure; and a mixture of N-acetylated human angiotensin I and the reaction products obtained after post-treatment is dried.

(Charactrization of Reaction Products Resulted After Post-treatment)

The mixture of N-acetylated human angiotensin I and the reaction products resulted after post-treatment, prepared by conducting the series of chemical treatments as explained above, is subjected to mass spectrometry to measure the molecular weights of the individual peptides contained therein.

In the present Example, using a Time-of-Flight type mass spectrometer, specifically, MALDI-TOF-MS system, there are conducted, on the dried mixture sample (for C1/3 analysis), measurement of the masses of main ion species, which are reflecting the molecular weights of individual peptides, and their relative signal intensities, and subsequently comparison thereof. Mass spectrometry under the same conditions is conducted separately for the dried sample of N-acetylated human angiotensin I obtained from the pretreatment alone, to determine the mass of main ion species from N-acetylated human angiotensin I to be used as a reference.

FIG. 2 shows the mass spectrum measured for the mixture containing reaction products, which are treated for successively releasing C-terminal amino acids by said method of chemical treatment mentioned in the present Example. The mass of the main ion species from N-acetylated human angiotensin I is measured separately, referring to the measured mass for said peak, there are identified the reaction products corresponding to the important peaks measured in the mass spectrum of FIG. 2. In Table 1 are shown the masses of the peaks measured, their differences from the mass of the peak due to the original N-acetylated human angiotensin I, and the amino acid residues, which are removed in individual reaction products, identified based thereon, as well as the forms of individual reaction products.

TABLE 1

| m/Z | Δm | Assignment | Corresponding peptide structure |
|---|---|---|---|
| 1380.7 | +42.0 | +CH$_3$CO | Ac-DRVY(Ac)IHPFHL |
| 1338.7 | — | | Ac-DRVYIHPFHL |
| 1267.6 | −71.1 | −Leu, +CH$_3$CO | Ac-DRVY(Ac)IHPF |
| 1224.6 | −114.1 | −Leu | Ac-DRVYIHPFH |
| 1130.5 | −208.2 | −His•Leu, +CH$_3$CO | Ac-DRVY(Ac)IHPF |
| 1088.5 | −250.2 | −His•Leu | Ac-DRVYIHPF |
| 983.5 | −355.2 | −Phe•His•Leu, +CH$_3$CO | Ac-DRVY(Ac)IHP |
| 941.5 | −397.2 | −Phe•His•Leu | Ac-DRVYIHP |

The peak due to the original N-acetylated human angiotensin I is accompanied by a peak having a mass which is larger by 42. The latter peak is judged to be due to those being modified with additional acetyl group, i.e. those having the O-acetylation on the side chain of tyrosine (Tyr). Assuming that the remaining three peaks each accompanied by a peak having a mass which is larger by 42, are due to those products at C-terminal of which the amino acids are successively released, naturally occurring amino acid residues that will give rise to its deference in the masses measured are identify. Since no further releasing proceeds after the release of these three amino acids, the fourth amino acid residue from C-terminal is concluded to be proline. Incidentally, leucine (Leu) and isoleucine (Ile) have the same formula weight and cannot be distinguished from each other in analysis by mass spectrometry; however, in Table 1, they are expressed as leucine (Leu).

It is confirmed by the above verification experiment that by conducting the treatment for selectively releasing C-terminal amino acids according to the present invention, a series of reaction products wherein the C-terminal amino acids have been successively removed from the original peptide, are obtained under mild treatment conditions and the C-terminal amino acid sequence of the peptide can be analyzed at a high accuracy.

Example 2

In this Example, it was verified that there occurs no progress of side reaction that may result in serious problem even if the reaction temperature varies slightly during the reaction of successively releasing C-terminal amino acids, because mild treatment conditions are employed in the treatment technique for selectively releasing C-terminal amino acids according to the present invention. In particular, the treatment temperature employed for the reaction of releasing C-terminal amino acids, which is included in the series of chemical treatments described in Example 1; was changed from 40° C. to 50° C., and the reaction products obtained in these two case were compared with each other.

There were chosen the same procedure and conditions for each operation as the operational procedure and conditions described in Example 1, with the except of said change in the temperature for the reaction of releasing by using acetic anhydride with 5% by volume of trifluoroacetic acid added threreto.

Figure 3:
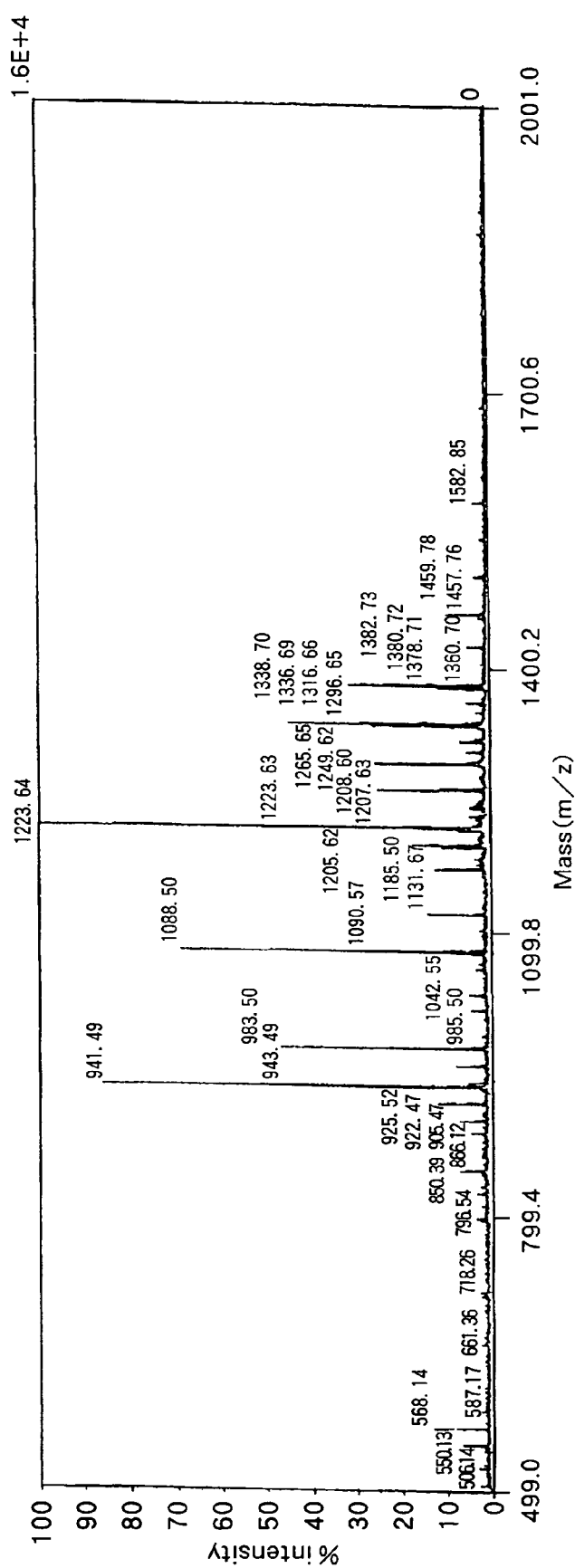
FIG. 3 shows another example of the spectra observed in mass spectrometric analysis of a mixture of reaction products, which are obtained by successively releasing the C-terminal amino acids from angiotensin I peptide according to said treatment method of the present invention for releasing C-terminal amino acids successively from the peptide.

FIG. 3 shows the mass spectrum measured for the mixture comprising reaction products, obtained by the treatment for successively releasing C-terminal amino acids in said way for chemical treatments as explained in the present example. Summarized in Table 2 are the results of assignment for reaction products corresponding to the important peaks measured in the mass spectrum of FIG. 3. Comparison between the spectrum of FIG. 3 and the spectrum of FIG. 2 confirms that even when the temperature for treatment of releasing is increased from 40° C. to 50° C., there is no further progress in removal after three amino acids from C-terminal has been removed and there occurs no side reaction such as cleavage in the middle of the peptide.

TABLE 2

| m/Z | Δm | Assignment | Corresponding peptide structure |
|---|---|---|---|
| 1380.7 | +42.0 | +CH$_3$CO | Ac-DRVY(Ac)IHPFHL |
| 1338.7 | — | | Ac-DRVYIHPFHL |
| 1265.7 | −73.0 | −Leu, +CH$_3$CO | Ac-DRVY(Ac)IHPFH |
| 1223.6 | −115.1 | −Leu | Ac-DRVYIHPFH |
| 1131.6 | −207.1 | −His•Leu, +CH$_3$CO | Ac-DRVY(Ac)IHPF |
| 1088.6 | −250.1 | −His•Leu | Ac-DRVYIHPF |
| 983.5 | −355.2 | −Phe•His•Leu, +CH$_3$CO | Ac-DRVY(Ac)IHP |
| 941.5 | −397.2 | −Phe•His•Leu | Ac-DRVYIHP |

Example 3

In said cases of Example 1 and Example 2, the pretreatment operation was carried out in order to modify the N-terminal amino group of peptide for its protection. In the present Example, it was verified that no side reaction causing serious troubles takes place even when the pretreatment is not carried out, because, in the process for the chemical treatment according to the present invention, at the step of carrying out the treatment of successively releasing C-terminal amino acids, a peptide sample used is dried up in advance into a solid phase, and the reaction is promoted by supplying both acetic anhydride and trifluoroacetic acid in a vapor phase, which are utilized in the reaction.

Specifically explaining, the pretreatment described in Example 1 was omitted, and the operation for the reaction of releasing C-terminal amino acids and the subsequent post-treatment operation were conducted to a dried sample of human angiotensin I. In this case, in the operation for the reaction of releasing C-terminal amino acids, the treatment temperature was selected at 50° C. as in Example 2.

In the operation, as acetic anhydride and trifluoroacetic acid are supplied in a vapor phase to give rise to a reaction, there proceed simultaneously, in addition to the reaction of releasing C-terminal amino acids, N-acetylation to the N-terminal amino group of peptide and O-acetylation to the phenolic hydroxy group on the side chain of tyrosine. Further, there occur such by-products that have modifications of trifluoroacetyl group to the N-terminal amino group of peptide and to the phenolic hydroxy group on the side chain of tyrosine therein, which is presumably attributable to such phenomena that when acting acetic anhydride and trifluoroacetic acid coincidently, the exchange reaction between these two may also occur.

Figure 4:
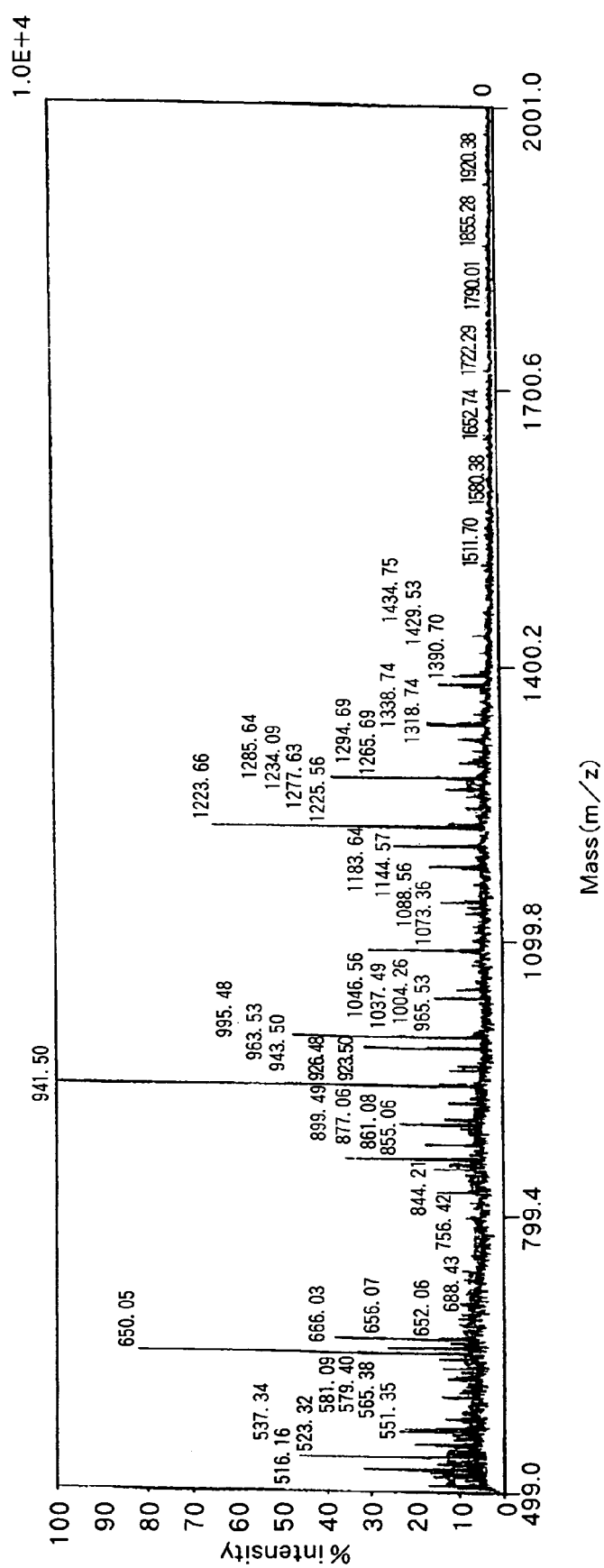
FIG. 4 shows still other example of the spectra observed in mass spectrometric analysis of a mixture of reaction products, which are obtained by successively releasing the C-terminal amino acids from angiotensin I peptide according to the treatment method of the present invention for releasing C-terminal amino acids successively from the peptide.

In FIG. 4 is shown the mass spectrum observed for the mixture containing reaction products resulted from the treatment for successively releasing C-terminal amino acids conducted by said method for chemical treatments as explained in the present example. In Table 3 are summarized the results of assignment for reaction products corresponding to the important peaks measured in the mass spectrum shown in FIG. 4. Comparison of the spectra of FIG. 4 and FIG. 3 confirms that, even when no pretreatment is conducted, N-acetylation to the N-terminal amino group of peptide proceeds as well simultaneously, no further removal takes place after the 3 amino acids from the C-terminal has been removed, and there is no side reaction such as cleavage in the middle of the peptide. Incidentally, the amide bonds for the N-terminal amino groups being modified with trifluoroacetyl group are partially hydrolyzed in the post-treatment with far more ease than those being modified with acetyl group; therefore, there is observed an accessory peak having a mass which is smaller by 42, corresponding to reaction products in which the N-terminal amino group is not N-acylated. That is, in Example 1 and Example 2, since modification by acetyl group is made to the N-terminal amino group of peptide in the pretreatment step, there is no reaction product in which the N-terminal amino group is modified with a trifluoroacetyl group in place of an acetyl group; however, in the present Example, there are also formed some portion of reaction products in which the N-terminal amino group are modified with a trifluoroacetyl group. In the spectrum of FIG. 4, there are indeed observed collateral peaks attributed to the modification of N-terminal amino group with trifluoroacetyl group, having a mass which is larger by 54 that of a peak due to that having the modification of N-terminal amino group with acetyl group.

TABLE 3

| m/Z | Δm | Assignment | Corresponding peptide structure |
|---|---|---|---|
| 1380.7 | +42.0 | +CH$_3$CO | Ac-DRVY(Ac)IHPFHL |
| 1338.7 | — | | Ac-DRVYIHPFHL |
| 1277.6 | −61.1 | −Leu+Δ(CF$_3$—CH$_3$) | Tf-DRVYIHPFH |
| 1265.7 | −73.0 | −Leu, +CH$_3$CO | Ac-DRVY(Ac)IHPFH |
| 1223.6 | −115.1 | −Leu | Ac-DRVYIHPFH |
| 1183.6 | −155.1 | −Leu−CH$_3$CO | DRVYIHPFH |
| 1088.6 | −250.1 | −His·Leu | Ac-DRVYIHPF |
| 1046.6 | −292.1 | −His·Leu−CH$_3$CO | DRVYIHPF |
| 993.5 | −345.2 | −Phe·His·Leu, +Δ(CF$_3$—CH$_3$) | Tf-DRVYIHP |
| 983.5 | −355.2 | −Phe·His·Leu, +CH$_3$CO | Ac-DRVY(Ac)IHP |
| 941.5 | −397.2 | −Phe·His·Leu | Ac-DRVYIHP |
| 899.5 | −439.2 | −Phe·His·Leu−CH$_3$CO | DRVYIHP |

Furthermore, it is clearly confirmed that, in addition to the N-acetylation to the N-terminal amino group of peptide, O-acetylation to the phenolic hydroxy group on the side chain of tyrosine proceeds simultaneously. Meanwhile, as the reaction is practiced in a solid phase, there are effectively avoided such undesired side reactions that the activated reaction intermediates, for example asymmetric acid anhydride, formed in the reaction of successively releasing C-terminal amino acids, would act on the N-terminal amino group of peptide and the phenolic hydroxy group on the side chain of tyrosine. In contrast, the N-acetylation and O-acetylation effected by the acetic anhydride and trifluoroacetic acid both supplied in a vapor phase progress rapidly. As a result, it is confirmed that the reaction of successively releasing C-terminal amino acids proceeds in such state that the peptide has been in situ modified for its protection.

INDUSTRIAL APPLICABILITY

In the method for analysis of C-terminal amino acid sequence of peptide according to the present invention, as the means for successively releasing the C-terminal amino acids of peptide, employed is such technique comprising steps of allowing the alkanoic acid anhydride and perfluoroalkanoic acid both of vapor phase, supplied from a mixture obtained by adding a small amount of an alkanoic acid anhydride to a perfluoroalkanoic acid, to act on a peptide to be examined of dried solid state in a dry atmosphere at a temperature selected in a range of 10 to 60° C., and and carrying out the release of the C-terminal amino acid in association with the process that formation of a 5-oxazolone structure thereof is followed by the cleavage of the 5-oxazolone ring to prepare a series of reaction products. In this technique, since the alkanoic acid anhydride used per se has a low reactivity, it is possible to successively release the C-terminal amino acids of peptide under a mild temperature condition such as a temperature selected in a range of 15 to 60° C., preferably room temperature or a temperature slightly higher than that, for instance, a temperature selected in a range of 15 to 50° C., without inviting undesired side reactions such as cleavage of amide bond in the middle of peptide. In this connection, since there is no cleavage of amide bond in the middle of peptide, it is feasible to avoid mixing the peptide fragment resulting from said cleavage of amide bond and the reaction product originating from the peptide fragment in the aimed reaction products obtained. Furthermore, with use of the reaction under such a mild condition, it is possible to attain more superior adjustment and control of the maximum length of the amino acids to be cut off for the C-terminal amino acid sequencing. Therefore, in the light of such merits as the excellent controllability and the mild reaction conditions, for instance the wide range of admittable variation in reaction temperature in the process for successively releasing the C-terminal amino acids of peptide, the method for analysis of the C-terminal amino acid sequence of peptide according to the present invention comes up to an analytical method having wide applicability.

The invention claimed is:

1. A method for analyzing the C-terminal amino acid sequence of a peptide to be examined, which method comprises steps of:
    releasing the C-terminal amino acids in sequence from the peptide to be examined by chemical means to prepare a mixture containing a series of reaction products thereof,
    subjecting the series of reaction products and the original peptide to mass spectrometry to measure the decreases in molecular weight associated with the successive release of the C-terminal amino acid thereof, and
    identifying a series of the amino acids removed successively, based on a series of the decrease in the molecular weight measured and arranging the amino acids identified from the C-terminal to obtain the information of the C-terminal amino acid sequence of the peptide,
    wherein the technique of treatment used in the step of releasing the C-terminal amino acids is a means comprising steps of:
    allowing an alkanoic acid anhydride and a perfluoroalkanoic acid both of vapor phase, which are supplied from a mixture containing an alkanoic acid anhydride with a small amount of a perfluoroalkanoic acid added thereto, to act on a dry sample of the peptide to be examined in a dry atmosphere at a temperature selected in a range of 15 to 60° C.; and carrying out the release of the C-terminal amino acid in association with the process that at the C-terminal of the peptide, the formation of a 5-oxazolone structure represented by the following general formula (III):

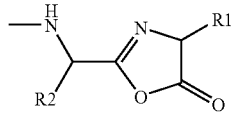

(III)

wherein R1 is a side chain of the C-terminal amino acid of the peptide, and R2 is a side chain of the amino acid residue positioned just before the C-terminal amino acid, is followed by the cleavage of the 5-oxazolone ring.

2. A method claimed in claim 1, wherein, in addition to the step of said treatment using the mixture obtained by adding a small amount of the perfluoroalkanoic acid to the alkanoic acid anhydride, the method is provided, prior to the step of releasing the C-terminal amino acids successively, with an additional step for a pre-treatment of applying, to the N-terminal amino group of the peptide to be examined, N-acylation protection in advance with use of an acyl group derived from the alkanoic acid constituting said alkanoic acid anhydride;
    wherein the pretreatment step of applying N-acylation protection to the N-terminal amino group is conducted by employing a technique where the N-acylation for amino groups in the peptide is effected by allowing an alkanoic acid anhydride and an alkanoic acid both of vapor phase, which are supplied from a mixture obtained by adding a small amount of the alkanoic acid to the alkanoic acid anhydride, to act on a dried sample of the peptide to be examined in a dry atmosphere at a temperature selected in a range of 10 to 60° C.

3. A method claimed in claim 2, wherein a symmetric anhydride of an alkanoic acid having 2 to 4 carbon atoms is used as the alkanoic acid anhydride contained in said mixture obtained by adding a small amount of a perfluoroalkanoic acid to the alkanoic acid anhydride.

4. A method claimed in claim 3, wherein a symmetric anhydride of a linear-chain alkanoic acid having 2 to 4 carbon atoms is used as said symmetric anhydride of an alkanoic acid having 2 to 4 carbon atoms.

5. A method claimed in claim 2, wherein acetic anhydride is used as the alkanoic acid anhydride contained in said mixture obtained by adding a small amount of a perfluoroalkanoic acid to the alkanoic acid anhydride.

6. A method claimed in claim 2, wherein a perfluoroalkanoic acid of which pKa is within the range of 0.3 to 2.5 is used as the perfluoroalkanoic acid contained in said mixture obtained by adding a small amount of the perfluoroalkanoic acid to the alkanoic acid anhydride.

7. A method claimed in claim 2, wherein a perfluoroalkanoic acid having 2 to 4 carbon atoms is used as the perfluoroalkanoic acid contained in said mixture obtained by adding a small amount of the perfluoroalkanoic acid to the alkanoic acid anhydride.

8. A method claimed in claim 7, wherein a linear-chain perfluoroalkanoic acid having 2 to 4 carbon atoms is used as said perfluoroalkanoic acid having 2 to 4 carbon atoms.

9. A method claimed in claim 2, wherein in said mixture obtained by adding a small amount of the perfluoroalkanoic acid to the alkanoic acid anhydride, the content of the perfluoroalkanoic acid is selected in a range of 1 to 20% by volume relative to the total volume of the alkanoic acid anhydride and the perfluoroalkanoic acid.

10. A method claimed in claim 2, wherein, in the treatment using said mixture obtained by adding a small amount of the perfluoroalkanoic acid to the alkanoic acid anhydride, said dry atmosphere is a state in which oxygen as well as water has been removed.

11. A method claimed in claim 10, wherein the dry atmosphere is achieved inside an airtight vessel by vacuuming up the atmosphere inside it.

12. A method claimed in claim 2, wherein, in the treatment using the mixture obtained by adding a small amount of the perfluoroalkanoic acid to the alkanoic acid anhydride, the temperature is set at a temperature selected in a range of 15 to 50° C.

13. A method claimed in claim 2, wherein, in addition to the step of the treatment using said mixture obtained by adding a small amount of the perfluoroalkanoic acid to the alkanoic acid anhydride, the method is provided with additional steps for hydrolysis treatment comprising steps of:
    applying, to the mixture containing a series of reaction products, which is obtained in said step of releasing the C-terminal amino acids successively, a post-treatment of removing the residual alkanoic acid anhydride and perfluoroalkanoic acid therein in a dry state,
    then, feeding a basic, nitrogen-containing aromatic cyclic compound or a tertiary amine compound and water molecule both of vapor phase supplied by using an aqueous solution in which the basic, nitrogen-containing aromatic cyclic compound or a tertiary amine compound is dissolved, allowing the water molecule to act on the reaction products of peptide in the presence of said basic, nitrogen-containing organic compound, and after said treatment for hydrolysis, re-drying post-treatment which is conducted by removing the basic, nitrogen-containing organic compound and water molecule both remaining in the mixture containing a series of the reaction products, followed by drying.

14. A method claimed in claim 2, wherein as the alkanoic acid anhydride used in the pretreatment step of applying N-acylation protection to the N-terminal and as the alkanoic acid anhydride used in the step conducted thereafter of releasing the C-terminal amino acids successively, used is the same alkanoic acid anhydride.

15. A process for preparation of a mixture containing a series of reaction products obtainable by releasing the C-terminal amino acids successively from a target peptide with use of chemical means,
wherein the process is conducted to prepare the mixture containing a series of reaction products obtainable by releasing the C-terminal amino acids successively from the peptide by the chemical means comprising steps of:
allowing an alkanoic acid anhydride and a perfluoroalkanoic acid both of vapor phase, which are supplied from a mixture of the alkanoic acid anhydride with a small amount of the perfluoroalkanoic acid added thereto, to act on a dried sample of the target peptide in a dry atmosphere at a temperature selected in a range of 15 to 60° C., and
carrying out the release of the C-terminal amino acid in association with the process that at the C-terminal of the peptide, the formation of a 5-oxazolone structure represented by the following general formula (III):

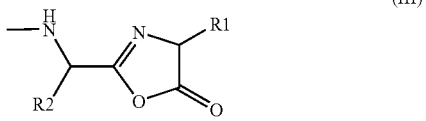

(III)

wherein R1 is a side chain of the C-terminal amino acid of the peptide, and R2 is a side chain of the amino acid residue positioned just before said C-terminal amino acid, is followed by the cleavage of the 5-oxazolone ring.

16. A kit used for treatment of reaction to release the C-terminal amino acids successively from a target peptide by chemical means according to the process as claimed in claim 15,
wherein the kit for treatment of releasing the C-terminal amino acids successively is the kit being set up with a combination of:
a liquid reagent for the reaction of releasing the C-terminal amino acids successively, at least a mixture obtained by adding a small amount of a perfluoroalkanoic acid to an alkanoic acid anhydride, or separately the alkanoic acid anhydride and the perfluoroalkanoic acid in combination for preparation of the mixture, wherein said mixture is used as the liquid reagent for the reaction of releasing the C-terminal amino acids successively,
a sample container for holding a sample of the target peptide to be treated therein, and
a reactor vessel which is provided with a liquid reagent-holding system capable of reserving said liquid reagent therein and capable of maintaining such a state that said liquid reagent makes no direct contact with said peptide sample held in the sample container and which has capacity to accommodate said sample container inside.

17. A process claimed in claim 15, wherein, in addition to the step of said treatment using the mixture obtained by adding a small amount of the perfluoroalkanoic acid to the alkanoic acid anhydride, the method is provided, prior to the step of releasing the C-terminal amino acids successively, with an additional step of releasing the C-terminal amino acids successively, with an additional step for a pre-treatment of applying, to the N-terminal amino group of the peptide to be examined, N-acylation protection in advance with use of an acyl group derived from the alkanoic acid constituting said alkanoic acid anhydride
wherein the pretreatment step of applying N-acylation protection to the N-terminal amino group is conducted by employing technique where the N-acylation for amino groups in the peptide is effected by allowing an alkanoic acid anhydride and an alkanoic acid both of vapor phase, which are supplied from a mixture obtained by adding a small amount of the alkanoic acid to the alkanoic acid anhydride, to act on a dried sample of the peptide to be examined in a dry atmosphere at a temperature selected in a range of 10 to 60° C.

18. A process claimed in claim 17, wherein, in addition to the step of the treatment using said mixture obtained by adding a small amount of the perfluoroalkanoic acid to the alkanoic acid anhydride, the method is provided with additional steps for hydrolysis treatment comprising steps of:
applying, to the mixture containing a series of reaction products, which is obtained in said step of releasing the C-terminal amino acids successively, a post-treatment of removing the residual alkanoic acid anhydride and perfluoroalkanoic acid therein in a dry state.
then, feeding a basic, nitrogen-containing aromatic cyclic compound or a tertiary amine compound and water molecule both of vapor phase supplied by using an aqueous solution in which the basic, nitrogen-containing aromatic cyclic compound or a tertiary amine compound is dissolved,
allowing the water molecule to act on the reaction products of peptide in the presence of said basic, nitrogen-containing organic compound, and
after said treatment for hydrolysis, re-drying post-treatment which is conducted by removing the basic, nitrogen-containing organic compound and water molecule both remaining in the mixture containing a series of the reaction products, followed by drying.

* * * * *